United States Patent
Zeroni et al.

(10) Patent No.: US 10,952,762 B2
(45) Date of Patent: Mar. 23, 2021

(54) MATERIAL REMOVAL DEVICE AND METHOD OF USE

(71) Applicant: Covidien LP, Mansfield, MA (US)

(72) Inventors: Jenny Zeroni, Plymouth, MN (US); Robert VanPelt, Jr., Saint Paul, MN (US); Cory Sills, Plymouth, MN (US); Scott Petersen, Brooklyn Park, MN (US); Nick van der Lugt, Eagan, MN (US)

(73) Assignee: Covidien LP, Mansfield, MA (US)

( * ) Notice: Subject to any disclaimer, the term of this patent is extended or adjusted under 35 U.S.C. 154(b) by 399 days.

(21) Appl. No.: 15/632,516

(22) Filed: Jun. 26, 2017

(65) Prior Publication Data

US 2017/0290604 A1 Oct. 12, 2017

Related U.S. Application Data

(63) Continuation of application No. 14/573,286, filed on Dec. 17, 2014, now Pat. No. 9,717,520, which is a
(Continued)

(51) Int. Cl.
*A61B 17/3207* (2006.01)
*A61B 17/00* (2006.01)
(Continued)

(52) U.S. Cl.
CPC .......... *A61B 17/320758* (2013.01); *A61B 2017/00685* (2013.01); *A61B 2017/22038* (2013.01);
(Continued)

(58) Field of Classification Search
CPC .... A61B 17/320758; A61B 17/320783; A61B 17/320791; A61B 2017/320766;
(Continued)

(56) References Cited

U.S. PATENT DOCUMENTS

| 1,481,078 A | 1/1924 | Albertson |
| 2,178,790 A | 11/1939 | Henry |
| (Continued) | | |

FOREIGN PATENT DOCUMENTS

| CA | 2000621 | 10/1989 |
| CN | 101795630 A | 8/2010 |
| (Continued) | | |

OTHER PUBLICATIONS

Amplatz Coronary Catheters, posted: Feb. 25, 2009, [online], [retrieved on Mar. 29, 2011], retrieved from the Cardiophile MD using Internet website <URL:http://cardiophile.org/2009/02/amplatzcoronary-catheter.html> (3 pages).

(Continued)

*Primary Examiner* — Kathleen S Holwerda
*Assistant Examiner* — Kankindi Rwego
(74) *Attorney, Agent, or Firm* — Stinson LLP

(57) ABSTRACT

An atherectomy catheter having an inner shaft which rotates a distal rotary tissue borer with a helical cutting surface which enables the catheter to out it and cross a CTO. Additionally, the atherectomy catheter has a distal cutting element rotated by an outer drive shaft configured to cut material from the wall of a vessel at a treatment site as the catheter is pushed distally through the treatment site. The atherectomy catheter includes a collection chamber positioned proximally of the cutting element and rotary tissue borer. The atherectomy catheter may include means to direct material cut from the treatment site into the collection chamber, means to break down larger portions of material that may block or clog the collection chamber and means of transporting the material collected from the treatment site to a proximal opening in the atherectomy catheter.

20 Claims, 21 Drawing Sheets

Related U.S. Application Data continuation of application No. 13/283,160, filed on Oct. 27, 2011, now Pat. No. 8,920,450.

(60) Provisional application No. 61/407,788, filed on Oct. 28, 2010.

(51) Int. Cl.
*A61B 17/22* (2006.01)
*A61B 17/32* (2006.01)

(52) U.S. Cl.
CPC .............. *A61B 2017/22039* (2013.01); *A61B 2017/22079* (2013.01); *A61B 2017/22094* (2013.01); *A61B 2017/320064* (2013.01); *A61B 2017/320766* (2013.01); *A61B 2017/320775* (2013.01)

(58) Field of Classification Search
CPC ....... A61B 2017/320775; A61B 2017/320064; A61B 2017/22079; A61B 17/32003; A61B 17/320036; A61B 17/3207; A61B 2017/320024; A61B 2017/320028; A61B 2017/320032; A61B 2017/320036; A61B 10/02; A61B 10/0233; A61B 10/0241; A61B 10/025; A61B 10/0266; A61B 10/0275; A61B 10/0283; A61B 10/0291; A61B 2010/0208; A61B 2010/0216; A61B 2010/0225; A61B 2010/0258; A61F 9/00736; A61F 9/00763
USPC .................................. 606/170, 180; 600/567
See application file for complete search history.

(56) References Cited

U.S. PATENT DOCUMENTS

| | | | |
|---|---|---|---|
| 2,701,559 A | 2/1955 | Cooper |
| 2,850,007 A | 9/1958 | Lingley |
| 3,064,651 A | 11/1962 | Henderson |
| 3,082,805 A | 3/1963 | Royce |
| 3,320,957 A | 5/1967 | Sokolik |
| 3,614,953 A | 10/1971 | Moss |
| 3,683,891 A | 8/1972 | Eskridge et al. |
| 3,705,577 A | 12/1972 | Sierra |
| 3,732,858 A | 5/1973 | Banko |
| 3,749,085 A | 7/1973 | Willson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,273,128 A | 6/1981 | Lary |
| 4,306,562 A | 12/1981 | Osborne |
| 4,306,570 A | 12/1981 | Matthews |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,601,290 A * | 7/1986 | Effron .............. A61B 17/32002 606/170 |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A * | 3/1987 | Thimsen .......... A61B 17/32002 30/133 |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom et al. |
| 4,706,671 A | 11/1987 | Weinrib |
| 4,728,319 A | 3/1988 | Masch |
| 4,729,763 A | 3/1988 | Henrie |
| 4,730,616 A | 3/1988 | Frisbie et al. |
| 4,732,154 A | 3/1988 | Shiber |
| 4,733,662 A | 3/1988 | DeSatnick et al. |
| 4,745,919 A | 5/1988 | Bundy et al. |
| 4,747,406 A | 5/1988 | Nash |
| 4,747,821 A | 5/1988 | Kensey et al. |
| 4,749,376 A | 6/1988 | Kensey et al. |
| 4,754,755 A | 7/1988 | Husted |
| 4,757,819 A | 7/1988 | Yokoi et al. |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMicheal et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinski et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |

(56) References Cited

U.S. PATENT DOCUMENTS

| | | |
|---|---|---|
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,064,435 A | 11/1991 | Porter |
| 5,071,425 A | 12/1991 | Gifford, III et al. |
| 5,074,841 A | 12/1991 | Ademovic et al. |
| 5,077,506 A | 12/1991 | Krause |
| 5,078,722 A | 1/1992 | Stevens |
| 5,078,723 A | 1/1992 | Dance et al. |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kipperman |
| 5,092,873 A | 3/1992 | Simpson et al. |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |
| 5,110,822 A | 5/1992 | Sherba et al. |
| 5,112,345 A | 5/1992 | Farr |
| 5,114,399 A | 5/1992 | Kovalcheck |
| 5,115,814 A | 5/1992 | Griffith et al. |
| 5,120,323 A | 6/1992 | Shockey et al. |
| 5,127,902 A | 7/1992 | Fischell |
| 5,127,917 A | 7/1992 | Niederhauser et al. |
| 5,135,531 A | 8/1992 | Shiber |
| 5,154,705 A | 10/1992 | Fleischhacker et al. |
| 5,154,724 A | 10/1992 | Andrews |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,183,432 A | 2/1993 | Noguchi |
| 5,190,528 A | 3/1993 | Fonger et al. |
| 5,192,291 A | 3/1993 | Pannek, Jr. |
| 5,195,956 A | 3/1993 | Stockmeier |
| 5,211,651 A | 5/1993 | Reger et al. |
| 5,217,474 A | 6/1993 | Zacca et al. |
| 5,222,966 A | 6/1993 | Perkins et al. |
| 5,224,488 A | 7/1993 | Neuffer |
| 5,224,945 A | 7/1993 | Pannek, Jr. |
| 5,224,949 A | 7/1993 | Gomringer et al. |
| 5,226,909 A | 7/1993 | Evans et al. |
| 5,226,910 A | 7/1993 | Kajiyama et al. |
| 5,234,451 A | 8/1993 | Osypka |
| 5,242,460 A | 9/1993 | Klein et al. |
| 5,242,461 A | 9/1993 | Kortenbach et al. |
| 5,250,059 A | 10/1993 | Andreas et al. |
| 5,250,065 A | 10/1993 | Clement et al. |
| 5,263,928 A | 11/1993 | Trauthen et al. |
| 5,263,959 A | 11/1993 | Fischell |
| 5,267,955 A | 12/1993 | Hanson |
| 5,267,982 A | 12/1993 | Sylvanowicz |
| 5,269,793 A | 12/1993 | Simpson |
| 5,273,526 A | 12/1993 | Dance et al. |
| 5,282,484 A | 2/1994 | Reger |
| 5,284,486 A | 2/1994 | Kotula et al. |
| 5,285,795 A | 2/1994 | Ryan et al. |
| 5,286,253 A * | 2/1994 | Fucci ............... A61B 17/32002 604/22 |
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,312,425 A | 5/1994 | Evans et al. |
| 5,312,427 A | 5/1994 | Shturman |
| 5,314,438 A | 5/1994 | Shturman |
| 5,318,032 A | 6/1994 | Lonsbury et al. |
| 5,318,528 A | 6/1994 | Heaven et al. |
| 5,318,576 A | 6/1994 | Plassche, Jr. et al. |
| 5,321,501 A | 6/1994 | Swanson et al. |
| 5,322,508 A | 6/1994 | Viera |
| 5,334,211 A | 8/1994 | Shiber |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,360,432 A | 11/1994 | Shturman |
| 5,366,463 A | 11/1994 | Ryan |
| 5,368,035 A | 11/1994 | Hamm et al. |
| 5,370,609 A | 12/1994 | Drasler et al. |
| 5,370,651 A | 12/1994 | Summers |
| 5,372,601 A | 12/1994 | Lary |
| 5,372,602 A | 12/1994 | Burke |
| 5,373,619 A | 12/1994 | Fleischhacker et al. |
| 5,373,849 A | 12/1994 | Maroney et al. |
| 5,377,682 A | 1/1995 | Ueno et al. |
| 5,378,234 A | 1/1995 | Hammerslag et al. |
| 5,383,460 A | 1/1995 | Jang et al. |
| 5,395,311 A | 3/1995 | Andrews |
| 5,395,313 A | 3/1995 | Naves et al. |
| 5,395,335 A | 3/1995 | Jang |
| 5,397,345 A | 3/1995 | Lazarus |
| 5,402,790 A | 4/1995 | Jang et al. |
| 5,403,334 A | 4/1995 | Evans et al. |
| 5,409,454 A | 4/1995 | Fischell et al. |
| 5,413,107 A | 5/1995 | Oakley et al. |
| 5,419,774 A | 5/1995 | Willard et al. |
| 5,423,740 A | 6/1995 | Sullivan et al. |
| 5,423,799 A | 6/1995 | Shiu |
| 5,423,838 A | 6/1995 | Willard |
| 5,423,846 A | 6/1995 | Fischell |
| 5,427,107 A | 6/1995 | Milo et al. |
| 5,429,136 A | 7/1995 | Milo et al. |
| 5,431,673 A | 7/1995 | Summers et al. |
| 5,441,510 A | 8/1995 | Simpson et al. |
| 5,443,446 A | 8/1995 | Shturman |
| 5,443,497 A | 8/1995 | Venbrux |
| 5,444,078 A | 8/1995 | Yu et al. |
| 5,445,155 A | 8/1995 | Sieben |
| 5,449,369 A | 9/1995 | Imran |
| 5,451,233 A | 9/1995 | Yock |
| 5,454,809 A | 10/1995 | Janssen |
| 5,456,667 A | 10/1995 | Ham et al. |
| 5,456,689 A | 10/1995 | Kresch et al. |
| 5,458,585 A | 10/1995 | Salmon et al. |
| 5,459,570 A | 10/1995 | Swanson et al. |
| 5,464,016 A | 11/1995 | Nicholas et al. |
| 5,470,415 A | 11/1995 | Perkins et al. |
| 5,485,042 A | 1/1996 | Burke |
| 5,485,840 A | 1/1996 | Bauman |
| 5,487,729 A | 1/1996 | Avellanet et al. |
| 5,489,295 A | 2/1996 | Piplani et al. |
| 5,491,524 A | 2/1996 | Hellmuth et al. |
| 5,496,267 A | 3/1996 | Drasler et al. |
| 5,501,694 A | 3/1996 | Ressemann et al. |
| 5,503,155 A | 4/1996 | Salmon et al. |
| 5,505,210 A | 4/1996 | Clement |
| 5,507,292 A | 4/1996 | Jang |
| 5,507,760 A | 4/1996 | Wynne et al. |
| 5,507,761 A | 4/1996 | Duer |
| 5,507,795 A | 4/1996 | Chiang et al. |
| 5,512,044 A | 4/1996 | Duer |
| 5,514,115 A | 5/1996 | Frantzen et al. |
| 5,520,189 A | 5/1996 | Malinowski et al. |
| 5,522,825 A | 6/1996 | Kropf et al. |
| 5,522,880 A | 6/1996 | Barone et al. |
| 5,527,292 A | 6/1996 | Adams et al. |
| 5,527,298 A | 6/1996 | Vance et al. |
| 5,527,325 A | 6/1996 | Conley et al. |
| 5,531,685 A | 7/1996 | Hemmer et al. |
| 5,531,690 A | 7/1996 | Solar |
| 5,531,700 A | 7/1996 | Moore et al. |
| 5,540,707 A | 7/1996 | Ressemann et al. |
| 5,549,601 A | 8/1996 | McIntyre et al. |
| 5,554,163 A | 9/1996 | Shturman |
| 5,556,408 A | 9/1996 | Farhat |
| 5,558,093 A | 9/1996 | Pomeranz |
| 5,562,726 A | 10/1996 | Chuter |
| 5,562,728 A | 10/1996 | Lazarus et al. |
| 5,569,275 A | 10/1996 | Kotula et al. |
| 5,569,276 A | 10/1996 | Jang et al. |

(56) References Cited

U.S. PATENT DOCUMENTS

| | | | |
|---|---|---|---|
| 5,569,277 | A | 10/1996 | Evans et al. |
| 5,569,279 | A | 10/1996 | Rainin |
| 5,569,284 | A * | 10/1996 | Young ............... A61B 17/32002 606/180 |
| 5,570,693 | A | 11/1996 | Jang et al. |
| 5,571,122 | A | 11/1996 | Kelly et al. |
| 5,571,130 | A | 11/1996 | Simpson et al. |
| 5,575,817 | A | 11/1996 | Martin |
| 5,584,842 | A | 12/1996 | Fogarty et al. |
| 5,584,843 | A | 12/1996 | Wulfman et al. |
| 5,609,605 | A | 3/1997 | Marshall et al. |
| 5,618,293 | A | 4/1997 | Sample et al. |
| 5,620,447 | A | 4/1997 | Smith et al. |
| 5,624,457 | A | 4/1997 | Farley et al. |
| 5,626,562 | A | 5/1997 | Castro |
| 5,626,576 | A | 5/1997 | Janssen |
| 5,628,761 | A | 5/1997 | Rizik |
| 5,632,754 | A | 5/1997 | Farley et al. |
| 5,632,755 | A | 5/1997 | Nordgren et al. |
| 5,634,464 | A | 6/1997 | Jang et al. |
| 5,643,296 | A | 7/1997 | Hundertmark et al. |
| 5,643,298 | A | 7/1997 | Nordgren et al. |
| 5,649,941 | A | 7/1997 | Lary |
| 5,660,180 | A | 8/1997 | Malinowski et al. |
| 5,662,671 | A | 9/1997 | Barbut et al. |
| 5,665,098 | A | 9/1997 | Kelly et al. |
| 5,669,920 | A | 9/1997 | Conley et al. |
| 5,674,232 | A | 10/1997 | Halliburton |
| 5,676,696 | A | 10/1997 | Marcade |
| 5,676,697 | A | 10/1997 | McDonald |
| 5,681,336 | A | 10/1997 | Clement et al. |
| 5,682,897 | A | 11/1997 | Pomeranz |
| 5,683,449 | A | 11/1997 | Marcade |
| 5,683,453 | A | 11/1997 | Palmaz |
| 5,688,234 | A | 11/1997 | Frisbie |
| 5,695,506 | A | 12/1997 | Pike et al. |
| 5,695,507 | A | 12/1997 | Auth et al. |
| 5,697,944 | A | 12/1997 | Lary |
| 5,700,240 | A | 12/1997 | Barwick, Jr. et al. |
| 5,700,687 | A | 12/1997 | Finn |
| 5,707,350 | A | 1/1998 | Krause et al. |
| 5,707,376 | A | 1/1998 | Kavteladze et al. |
| 5,707,383 | A | 1/1998 | Bays et al. |
| 5,709,698 | A | 1/1998 | Adams et al. |
| 5,713,913 | A | 2/1998 | Lary et al. |
| 5,715,825 | A | 2/1998 | Crowley |
| 5,716,410 | A | 2/1998 | Wang et al. |
| 5,720,735 | A | 2/1998 | Dorros |
| 5,724,977 | A | 3/1998 | Yock et al. |
| 5,728,123 | A | 3/1998 | Lemelson et al. |
| 5,733,296 | A | 3/1998 | Rogers et al. |
| 5,735,816 | A | 4/1998 | Lieber et al. |
| 5,741,270 | A | 4/1998 | Hansen et al. |
| 5,766,192 | A | 6/1998 | Zacca |
| 5,772,674 | A | 6/1998 | Nakhjavan |
| 5,775,327 | A | 7/1998 | Randolph et al. |
| 5,776,114 | A | 7/1998 | Frantzen et al. |
| 5,776,153 | A | 7/1998 | Rees |
| 5,779,643 | A | 7/1998 | Lum et al. |
| 5,779,673 | A | 7/1998 | Roth et al. |
| 5,779,721 | A | 7/1998 | Nash |
| 5,779,722 | A | 7/1998 | Shturman et al. |
| 5,792,157 | A | 8/1998 | Mische et al. |
| 5,797,949 | A | 8/1998 | Parodi |
| 5,799,655 | A | 9/1998 | Jang et al. |
| 5,807,329 | A | 9/1998 | Gelman |
| 5,810,867 | A | 9/1998 | Zarbatany et al. |
| 5,816,923 | A | 10/1998 | Milo et al. |
| 5,820,592 | A | 10/1998 | Hammerslag |
| 5,823,971 | A | 10/1998 | Robinson et al. |
| 5,824,039 | A | 10/1998 | Piplani et al. |
| 5,824,055 | A | 10/1998 | Spiridigliozzi et al. |
| 5,827,201 | A | 10/1998 | Samson et al. |
| 5,827,229 | A | 10/1998 | Auth et al. |
| 5,827,304 | A | 10/1998 | Hart |
| 5,827,322 | A | 10/1998 | Williams |
| 5,830,224 | A | 11/1998 | Cohn et al. |
| 5,836,957 | A | 11/1998 | Schulz et al. |
| 5,843,022 | A | 12/1998 | Willard et al. |
| 5,843,103 | A | 12/1998 | Wulfman |
| 5,843,161 | A | 12/1998 | Solovay |
| 5,855,563 | A | 1/1999 | Kaplan et al. |
| 5,865,748 | A | 2/1999 | Co et al. |
| 5,868,685 | A | 2/1999 | Powell et al. |
| 5,868,767 | A | 2/1999 | Farley et al. |
| 5,871,536 | A | 2/1999 | Lazarus |
| 5,873,882 | A | 2/1999 | Straub et al. |
| 5,876,414 | A * | 3/1999 | Straub ............ A61B 17/320783 606/159 |
| 5,879,397 | A | 3/1999 | Kalberer et al. |
| 5,883,458 | A | 3/1999 | Sumita et al. |
| 5,888,201 | A | 3/1999 | Stinson et al. |
| 5,895,399 | A | 4/1999 | Barbut et al. |
| 5,895,402 | A | 4/1999 | Hundertmark et al. |
| 5,902,245 | A | 5/1999 | Yock |
| 5,910,150 | A | 6/1999 | Saadat |
| 5,911,734 | A | 6/1999 | Tsugita et al. |
| 5,916,210 | A | 6/1999 | Winston |
| 5,922,003 | A | 7/1999 | Anctil et al. |
| 5,935,108 | A | 8/1999 | Katoh et al. |
| 5,938,645 | A | 8/1999 | Gordon |
| 5,938,671 | A | 8/1999 | Katoh et al. |
| 5,938,672 | A | 8/1999 | Nash |
| 5,941,869 | A | 8/1999 | Patterson et al. |
| 5,947,985 | A | 9/1999 | Imran |
| 5,948,184 | A | 9/1999 | Frantzen et al. |
| 5,951,480 | A | 9/1999 | White et al. |
| 5,951,482 | A | 9/1999 | Winston et al. |
| 5,954,745 | A | 9/1999 | Gertler et al. |
| 5,968,064 | A | 10/1999 | Selmon et al. |
| 5,972,019 | A | 10/1999 | Engelson et al. |
| 5,985,397 | A | 11/1999 | Witt et al. |
| 5,989,281 | A | 11/1999 | Barbut et al. |
| 5,997,557 | A | 12/1999 | Barbut et al. |
| 6,001,112 | A | 12/1999 | Taylor |
| 6,010,449 | A | 1/2000 | Selmon et al. |
| 6,010,522 | A | 1/2000 | Barbut et al. |
| 6,013,072 | A | 1/2000 | Winston et al. |
| 6,019,778 | A | 2/2000 | Wilson et al. |
| 6,022,362 | A | 2/2000 | Lee et al. |
| 6,027,450 | A | 2/2000 | Brown et al. |
| 6,027,460 | A | 2/2000 | Shturman |
| 6,027,514 | A | 2/2000 | Stine et al. |
| 6,032,673 | A | 3/2000 | Savage et al. |
| 6,036,646 | A | 3/2000 | Barthe et al. |
| 6,036,656 | A | 3/2000 | Slater |
| 6,036,707 | A | 3/2000 | Spaulding |
| 6,048,349 | A | 4/2000 | Winston et al. |
| 6,050,949 | A | 4/2000 | White et al. |
| 6,063,093 | A | 5/2000 | Winston et al. |
| 6,066,153 | A | 5/2000 | Lev |
| 6,068,603 | A | 5/2000 | Suzuki |
| 6,068,638 | A | 5/2000 | Makower |
| 6,081,738 | A | 6/2000 | Hinohara et al. |
| RE36,764 | E | 7/2000 | Zacca et al. |
| 6,095,990 | A | 8/2000 | Parodi |
| 6,099,542 | A | 8/2000 | Cohn et al. |
| 6,106,515 | A | 8/2000 | Winston et al. |
| 6,110,121 | A | 8/2000 | Lenker |
| 6,120,515 | A | 9/2000 | Rogers et al. |
| 6,120,516 | A | 9/2000 | Selmon et al. |
| 6,126,649 | A | 10/2000 | VanTassel et al. |
| 6,129,734 | A | 10/2000 | Shturman et al. |
| 6,134,003 | A | 10/2000 | Tearney et al. |
| 6,152,909 | A | 11/2000 | Bagaoisan et al. |
| 6,152,938 | A | 11/2000 | Curry |
| 6,156,046 | A | 12/2000 | Passafaro et al. |
| 6,157,852 | A | 12/2000 | Selmon et al. |
| 6,159,195 | A | 12/2000 | Ha et al. |
| 6,159,225 | A | 12/2000 | Makower |
| 6,165,127 | A | 12/2000 | Crowley |
| 6,165,188 | A | 12/2000 | Saadat et al. |
| 6,179,859 | B1 | 1/2001 | Bates et al. |
| 6,183,432 | B1 | 2/2001 | Milo |

(56) References Cited

U.S. PATENT DOCUMENTS

| | | |
|---|---|---|
| 6,187,025 B1 | 2/2001 | Machek |
| 6,190,353 B1 | 2/2001 | Makower et al. |
| 6,191,862 B1 | 2/2001 | Swanson et al. |
| 6,193,676 B1 | 2/2001 | Winston et al. |
| 6,196,963 B1 | 3/2001 | Williams |
| 6,206,898 B1 | 3/2001 | Honeycutt et al. |
| 6,217,527 B1 | 4/2001 | Selmon et al. |
| 6,217,549 B1 | 4/2001 | Selmon et al. |
| 6,217,595 B1 | 4/2001 | Shturman et al. |
| 6,221,049 B1 | 4/2001 | Selmon et al. |
| 6,221,332 B1 | 4/2001 | Thumm et al. |
| 6,228,049 B1 | 5/2001 | Schroeder et al. |
| 6,228,076 B1 | 5/2001 | Winston et al. |
| 6,231,546 B1 | 5/2001 | Milo et al. |
| 6,231,549 B1 | 5/2001 | Noecker et al. |
| 6,235,000 B1 | 5/2001 | Milo et al. |
| 6,238,405 B1 | 5/2001 | Findlay, III et al. |
| 6,241,667 B1 | 6/2001 | Vetter et al. |
| 6,241,744 B1 | 6/2001 | Imran et al. |
| 6,245,012 B1 | 6/2001 | Kleshinski |
| 6,258,052 B1 | 7/2001 | Milo |
| 6,263,236 B1 | 7/2001 | Kasinkas et al. |
| 6,264,611 B1 | 7/2001 | Ishikawa et al. |
| 6,266,550 B1 | 7/2001 | Selmon et al. |
| 6,277,138 B1 | 8/2001 | Levinson et al. |
| 6,283,951 B1 | 9/2001 | Flaherty et al. |
| 6,283,983 B1 | 9/2001 | Makower et al. |
| 6,299,622 B1 | 10/2001 | Snow et al. |
| 6,299,623 B1 | 10/2001 | Wulfman |
| 6,302,875 B1 | 10/2001 | Makower et al. |
| 6,305,834 B1 | 10/2001 | Schubert et al. |
| 6,312,444 B1 | 11/2001 | Barbut |
| 6,319,242 B1 | 11/2001 | Patterson et al. |
| 6,319,275 B1 | 11/2001 | Lashinski et al. |
| 6,330,884 B1 | 12/2001 | Kim |
| 6,355,005 B1 | 3/2002 | Powell et al. |
| 6,361,545 B1 | 3/2002 | Macoviak et al. |
| 6,375,615 B1 | 4/2002 | Flaherty et al. |
| 6,383,195 B1 | 5/2002 | Richard |
| 6,383,205 B1 | 5/2002 | Samson et al. |
| 6,394,976 B1 | 5/2002 | Winston et al. |
| 6,398,798 B2 | 6/2002 | Selmon et al. |
| 6,422,736 B1 | 7/2002 | Antoniades et al. |
| 6,423,081 B1 | 7/2002 | Lee et al. |
| 6,425,870 B1 | 7/2002 | Flesch |
| 6,428,551 B1 | 8/2002 | Hall et al. |
| 6,428,552 B1 | 8/2002 | Sparks |
| 6,443,966 B1 | 9/2002 | Shiu |
| 6,445,939 B1 | 9/2002 | Swanson et al. |
| 6,447,525 B2 | 9/2002 | Follmer et al. |
| 6,451,036 B1 | 9/2002 | Heitzmann et al. |
| 6,454,779 B1 | 9/2002 | Taylor |
| 6,475,226 B1 | 11/2002 | Belef et al. |
| 6,482,217 B1 | 11/2002 | Pintor et al. |
| 6,497,711 B1 | 12/2002 | Plaia et al. |
| 6,501,551 B1 | 12/2002 | Tearney et al. |
| 6,520,975 B2 | 2/2003 | Branco |
| RE38,018 E | 3/2003 | Anctil et al. |
| 6,532,380 B1 | 3/2003 | Close et al. |
| 6,533,749 B1 | 3/2003 | Mitusina et al. |
| 6,561,998 B1 | 5/2003 | Roth et al. |
| 6,565,588 B1 | 5/2003 | Clement et al. |
| 6,569,177 B1 | 5/2003 | Dillard et al. |
| 6,592,526 B1 | 7/2003 | Lenker |
| 6,620,180 B1 | 9/2003 | Bays et al. |
| 6,623,437 B2 | 9/2003 | Hinchliffe et al. |
| 6,623,495 B2 | 9/2003 | Findlay, III et al. |
| 6,623,496 B2 | 9/2003 | Snow et al. |
| 6,629,953 B1 | 10/2003 | Boyd |
| 6,638,233 B2 | 10/2003 | Corvi et al. |
| RE38,335 E | 11/2003 | Aust et al. |
| 6,652,505 B1 | 11/2003 | Tsugita |
| 6,652,548 B2 | 11/2003 | Evans et al. |
| 6,656,195 B2 | 12/2003 | Peters et al. |
| 6,666,874 B2 | 12/2003 | Heitzmann et al. |
| 6,682,543 B2 | 1/2004 | Barbut et al. |
| 6,733,511 B2 | 5/2004 | Hall et al. |
| 6,740,103 B2 | 5/2004 | Hall et al. |
| 6,746,462 B1 | 6/2004 | Selmon et al. |
| 6,764,495 B2 | 7/2004 | Lee et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfman et al. |
| 6,830,577 B2 | 12/2004 | Nash et al. |
| 6,843,797 B2 | 1/2005 | Nash et al. |
| 6,849,068 B1 | 2/2005 | Bagaoisan et al. |
| 6,863,676 B2 | 3/2005 | Lee et al. |
| 6,911,026 B1 | 6/2005 | Hall et al. |
| 6,970,732 B2 | 11/2005 | Winston et al. |
| 6,997,934 B2 | 2/2006 | Snow et al. |
| 7,153,315 B2 | 12/2006 | Miller |
| 7,172,610 B2 | 2/2007 | Heitzmann et al. |
| 7,208,511 B2 | 4/2007 | Williams et al. |
| 7,235,088 B2 | 6/2007 | Pintor et al. |
| 7,318,831 B2 | 1/2008 | Alvarez et al. |
| 7,388,495 B2 | 6/2008 | Fallin et al. |
| 7,479,148 B2 | 1/2009 | Beaupre |
| 7,488,322 B2 | 2/2009 | Brunnett et al. |
| 7,524,289 B2 | 4/2009 | Lenker |
| 7,603,166 B2 | 10/2009 | Casscells, III et al. |
| 7,708,749 B2 | 5/2010 | Simpson et al. |
| 7,713,235 B2 | 5/2010 | Torrance et al. |
| 7,713,279 B2 | 5/2010 | Simpson et al. |
| 7,729,745 B2 | 6/2010 | Maschke |
| 7,734,332 B2 | 6/2010 | Sher |
| 7,753,852 B2 | 7/2010 | Maschke |
| 7,758,599 B2 | 7/2010 | Snow et al. |
| 7,771,444 B2 | 8/2010 | Patel et al. |
| 7,887,556 B2 | 2/2011 | Simpson et al. |
| 2001/0000041 A1 | 3/2001 | Selmon et al. |
| 2001/0031784 A1 | 10/2001 | Petersen et al. |
| 2001/0031981 A1 | 10/2001 | Evans et al. |
| 2001/0044622 A1 | 11/2001 | Vardi et al. |
| 2001/0049500 A1 | 12/2001 | VanTassel et al. |
| 2002/0019644 A1 | 2/2002 | Hastings et al. |
| 2002/0022788 A1 | 2/2002 | Corvi et al. |
| 2002/0058904 A1 | 5/2002 | Boock et al. |
| 2002/0077373 A1 | 6/2002 | Hudson et al. |
| 2002/0077642 A1 | 6/2002 | Patel et al. |
| 2002/0095141 A1 | 7/2002 | Belef et al. |
| 2002/0103459 A1 | 8/2002 | Sparks et al. |
| 2002/0177800 A1 | 11/2002 | Bagaoisan et al. |
| 2002/0188307 A1 | 12/2002 | Pintor et al. |
| 2003/0018346 A1 | 1/2003 | Follmer et al. |
| 2003/0023263 A1 | 1/2003 | Krolik et al. |
| 2003/0078586 A1 | 4/2003 | Shapira |
| 2003/0093098 A1 | 5/2003 | Heitzmann et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2003/0163126 A1 | 8/2003 | West, Jr. |
| 2003/0199747 A1 | 10/2003 | Michlitsch et al. |
| 2003/0206484 A1 | 11/2003 | Childers et al. |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0167553 A1 | 8/2004 | Simpson et al. |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2005/0004585 A1 | 1/2005 | Hall et al. |
| 2005/0004594 A1 | 1/2005 | Nool et al. |
| 2005/0021063 A1 | 1/2005 | Hall et al. |
| 2005/0042239 A1 | 2/2005 | Lipiecki et al. |
| 2005/0090845 A1 | 4/2005 | Boyd |
| 2005/0090849 A1 | 4/2005 | Adams |
| 2005/0177068 A1 | 8/2005 | Simpson |
| 2005/0216018 A1 | 9/2005 | Sennett |
| 2005/0222596 A1 | 10/2005 | Maschke |
| 2005/0222663 A1 | 10/2005 | Simpson et al. |
| 2006/0015126 A1 | 1/2006 | Sher |
| 2006/0235334 A1 | 10/2006 | Corvi et al. |
| 2006/0259052 A1 | 11/2006 | Pintor et al. |
| 2007/0010840 A1 | 1/2007 | Rosenthal et al. |

(56) References Cited

U.S. PATENT DOCUMENTS

| | | |
|---|---|---|
| 2007/0038061 A1 | 2/2007 | Huennekens et al. |
| 2007/0049958 A1 | 3/2007 | Adams |
| 2007/0135712 A1 | 6/2007 | Maschke |
| 2007/0135886 A1 | 6/2007 | Maschke |
| 2007/0167824 A1 | 7/2007 | Lee et al. |
| 2007/0197996 A1* | 8/2007 | Kraft ............... A61B 10/025 604/500 |
| 2007/0225739 A1 | 9/2007 | Pintor et al. |
| 2007/0250096 A1* | 10/2007 | Yamane .............. A61B 17/22 606/159 |
| 2007/0265647 A1 | 11/2007 | Bonnette et al. |
| 2007/0276419 A1 | 11/2007 | Rosenthal |
| 2008/0001643 A1 | 1/2008 | Lee |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0045986 A1 | 2/2008 | To et al. |
| 2008/0051812 A1 | 2/2008 | Schmitz et al. |
| 2008/0065124 A1 | 3/2008 | Olson |
| 2008/0065125 A1 | 3/2008 | Olson |
| 2008/0097403 A1 | 4/2008 | Donaldson et al. |
| 2008/0125799 A1 | 5/2008 | Adams |
| 2008/0161840 A1 | 7/2008 | Osiroff et al. |
| 2008/0177139 A1 | 7/2008 | Courtney et al. |
| 2008/0208227 A1 | 8/2008 | Kadykowski et al. |
| 2008/0249553 A1 | 10/2008 | Gruber et al. |
| 2008/0312673 A1 | 12/2008 | Viswanathan et al. |
| 2009/0012548 A1 | 1/2009 | Thatcher et al. |
| 2009/0018565 A1 | 1/2009 | To et al. |
| 2009/0018566 A1 | 1/2009 | Escudero et al. |
| 2009/0138031 A1 | 5/2009 | Tsukernik |
| 2009/0187203 A1 | 7/2009 | Corvi et al. |
| 2009/0216125 A1 | 8/2009 | Lenker |
| 2009/0216180 A1 | 8/2009 | Lee et al. |
| 2009/0226063 A1 | 9/2009 | Rangwala et al. |
| 2009/0234378 A1 | 9/2009 | Escudero et al. |
| 2009/0270888 A1 | 10/2009 | Patel et al. |
| 2009/0275966 A1 | 11/2009 | Mitusina |
| 2009/0299394 A1 | 12/2009 | Simpson et al. |
| 2009/0306689 A1 | 12/2009 | Welty et al. |
| 2010/0030216 A1 | 2/2010 | Arcenio |
| 2010/0049225 A1 | 2/2010 | To et al. |
| 2010/0130996 A1 | 5/2010 | Doud et al. |
| 2010/0198240 A1 | 8/2010 | Simpson et al. |
| 2010/0241147 A1 | 9/2010 | Maschke |
| 2010/0280534 A1 | 11/2010 | Sher |
| 2010/0292721 A1 | 11/2010 | Moberg |
| 2010/0298850 A1 | 11/2010 | Snow et al. |
| 2010/0312263 A1 | 12/2010 | Moberg et al. |
| 2011/0004107 A1 | 1/2011 | Rosenthal et al. |
| 2011/0022069 A1 | 1/2011 | Mitusina |
| 2011/0040315 A1 | 2/2011 | To et al. |
| 2011/0130777 A1 | 6/2011 | Zhang et al. |
| 2011/0144673 A1 | 6/2011 | Zhang et al. |

FOREIGN PATENT DOCUMENTS

| | | |
|---|---|---|
| DE | 3732236 C1 | 9/1987 |
| DE | 8900059 | 1/1989 |
| DE | 9303531.4 | 3/1993 |
| DE | 1444166 A1 | 6/1996 |
| DE | 29722136 U1 | 4/1999 |
| EP | 0 086 048 A2 | 8/1983 |
| EP | 0 107 009 A2 | 5/1984 |
| EP | 0 229 620 A2 | 7/1987 |
| EP | 0 291 170 A1 | 11/1988 |
| EP | 0 302 701 A2 | 2/1989 |
| EP | 0 330 843 A1 | 9/1989 |
| EP | 0 373 927 A2 | 6/1990 |
| EP | 0 421 457 A1 | 4/1991 |
| EP | 0 431 752 A2 | 6/1991 |
| EP | 0 448 859 A2 | 10/1991 |
| EP | 0 463 798 A1 | 1/1992 |
| EP | 0 490 565 A1 | 6/1992 |
| EP | 0 514 810 A1 | 11/1992 |
| EP | 0 526 042 A1 | 2/1993 |
| EP | 0 533 320 A2 | 3/1993 |
| EP | 0 608 911 A1 | 8/1994 |
| EP | 0 608 912 A1 | 8/1994 |
| EP | 0 611 522 A1 | 8/1994 |
| EP | 0 648 414 A2 | 4/1995 |
| EP | 0 657 140 A1 | 6/1995 |
| EP | 0 680 695 A2 | 11/1995 |
| EP | 0 983 749 A2 | 3/2000 |
| EP | 1 767 159 A1 | 3/2007 |
| EP | 1 875 871 A2 | 1/2008 |
| GB | 2 093 353 A | 9/1982 |
| GB | 2 115 829 A | 9/1983 |
| GB | 2 210 965 A | 6/1989 |
| JP | 2-206452 | 8/1990 |
| JP | 2-271847 | 11/1990 |
| JP | 3-186256 | 8/1991 |
| JP | 04-200459 | 7/1992 |
| JP | 05-042162 | 2/1993 |
| JP | 05-056984 | 3/1993 |
| JP | 6-269460 | 9/1994 |
| JP | 1-75611 | 8/1995 |
| SU | 442795 | 9/1974 |
| SU | 665908 | 6/1979 |
| WO | 89/06517 | 7/1989 |
| WO | 9207500 | 5/1992 |
| WO | 93/13716 | 7/1993 |
| WO | 93/13717 | 7/1993 |
| WO | 93/16642 | 9/1993 |
| WO | 95/21576 | 8/1995 |
| WO | 96/11648 | 4/1996 |
| WO | 97/46164 | 12/1997 |
| WO | 98/04199 | 2/1998 |
| WO | 98/24372 | 6/1998 |
| WO | 99/39648 | 8/1999 |
| WO | 99/52454 | 10/1999 |
| WO | 00/30531 | 6/2000 |
| WO | 00/54735 | 9/2000 |
| WO | 00/62913 | 10/2000 |
| WO | 00/68300 | 11/2000 |
| WO | 00/72955 A1 | 12/2000 |
| WO | 01/15609 A1 | 3/2001 |
| WO | 01/19444 A1 | 3/2001 |
| WO | 01/30433 A1 | 5/2001 |
| WO | 01/43809 A1 | 6/2001 |
| WO | 01/43857 A1 | 6/2001 |
| WO | 02/16017 A2 | 2/2002 |
| WO | 02/45598 A2 | 6/2002 |
| WO | 2006/058223 A2 | 6/2006 |
| WO | 2006/066012 A2 | 6/2006 |

OTHER PUBLICATIONS

Judkins Left Coronary Catheter, posted: Feb. 19, 2009, [online], [retrieved on Mar. 29, 2011], retrieved from the Cardiophile MD using Internet website <URL:http://cardiophile.org/2009/02/judkins-left-coronary-catheter.html> (3 pages).

Huang et al., "Optical Coherence Tomography," Science, 254: 1178-1181 (1991).

Brezinski et al., "Optical Coherence Tomography for Optical Biopsy," Circulation, 93: 1206-1213 (1996).

Brezinski et al., "Assessing Atherosclerotic Plaque Morphology: Comparison of Optical Coherence Tomography and High Frequency Intravascular Ultrasound," Heart, 77:397-403 (1997).

Office Action dated Jun. 26, 2014 for Australian Application No. 2011319797, 3 pages, Woden Australia.

Canadian Office Action for Application No. 2,815,186 dated May 29, 2014, 3 pages, Canada.

Notice of Reasons for Rejection with English translation dated Mar. 20, 2014 for Japanese Application No. 2013-536829, 7 pages, Japan.

Office Action with English translation dated Jun. 27, 2014 for Korean Application No. 10-2013-7010686, 10 pages, Korea.

Office Action with English translation dated Apr. 14, 2014 for Russian Application No. 2013117043/14(025240), 6 pages, Russia.

(56) References Cited

OTHER PUBLICATIONS

International Search Report and Written Opinion dated Jan. 18, 2012 for corresponding PCT Application No. PCT/US2011/058107 (19 pages).
Office Action with English translation dated Oct. 28, 2014 for Chinese Application No. 201180052387.X, 17 pages, China.
Non-Final Office action for U.S. Appl. No. 14/573,286, dated Sep. 14, 2015, 10 pages.

* cited by examiner

MATERIAL REMOVAL DEVICE AND METHOD OF USE

This application is a continuation application of U.S. Ser. No. 14/573,286, filed Dec. 17, 2014, which is a continuation application of U.S. Ser. No. 13/283,160, issued as U.S. Pat. No. 8,920,450, filed Oct. 27, 2011, which claims the benefit of U.S. Provisional Patent Application No. 61/407,788, filed Oct. 28, 2010, entitled "Material Removal Device and Method of Use", the contents of each of which are hereby incorporated by reference herein.

FIELD OF THE INVENTION

The present invention relates to catheters used to remove and collect material from a treatment site in a body lumen. More particularly, this invention pertains to atherectomy catheters with dual drive shafts capable of crossing a totally occluded treatment site in a vessel to enable the catheter effectively treat the vessel at the treatment site.

BACKGROUND OF THE INVENTION

Atherosclerosis is a progressive disease of the vascular system whereby atheroma is deposited on the inner walls of blood vessels. Atherosclerosis is a complex, progressive and degenerative condition resulting in the build-up of cholesterol and other obstructive materials, known as plaque, on the walls of the arteries. The accumulation of plaque narrows the interior or lumen of arteries, thereby reducing blood flow.

Plaque occurs in the arteries in several different forms and may be located in many different anatomies throughout the arterial system. Plaque varies in composition, with portions that are hard and brittle, referred to as calcified plaque, and other portions that are fatty or fibrous. Over time atheromatous deposits become large enough to reduce or occlude blood flow through the vessels, leading to symptoms of low blood flow, such as pain in the legs (en walking or at rest), skin ulcer, angina (at rest or exertional), and other symptoms. To treat this disease and improve or resolve these symptoms it is desirable to restore or improve blood flow through the vessel.

Various means are used to restore or improve blood flow through atheromatous vessels. The atheroma deposits can be displaced by diametrically expanding the vessel by inflating balloons, expanding stents, and other methods. Such scar tissue (restenotic material), once formed, blocks flow in the vessel and often needs to be removed. The deposits can be pulverized using lasers and other methods however pulverization alone of atheromatous material may allow microemboli to flow downstream and lodge in distal vascular beds, further compromising blood flow to the tissue affected by the disease. Atherectomy catheters can be used to remove atheromatous deposits from the blood vessel and can present an ideal solution when the atheromatous debris removed from the vessel is captured and removed from the body.

Many types of atherectomy catheter devices have been proposed, including catheters with rotating burrs, lasers to photo-dissolve tissue, and catheters which use balloons or other positioning devices to position the cutter adjacent material to be removed.

Additionally, some catheters have a collection chamber positioned distally of the cutting window. This requires that the length of the catheter distal of the cutting window be long enough to accommodate the lection chamber. This creates some conflicting design choices. On the one hand, it is desirable for the collection chamber to have a capacity large enough to accommodate a reasonable amount of cut material before the chamber fills and the catheter must be removed. On the other hand, the increased length of the catheter distal to the cutting window necessary to accommodate a sufficiently large collection chamber is disadvantageous in certain applications. For example, if the treatment site or lesion is located in a vessel with a particularly tortuous anatomy or small size there might not be enough accessible vessel space distal to the lesion to accommodate the distal length of the catheter distal of the cutting window. This accessible space distal to the treatment site is sometimes referred to as the "landing zone". In order for the catheter to be used effectively the anatomy of the vessel must be such as to enable the catheter to be advanced far enough to position the cutting window within the treatment site and the distal portion of the catheter, which houses the collection chamber, in the landing zone. Thus, catheters having collection chambers located distally of the cutting window might be difficult to use in vessels with short landing zones.

In U.S. Provisional Patent Application 61/354,487 filed Jun. 14, 2010, the contents of which are incorporated herein by reference in their entirety, an atherectomy catheter which overcomes some of these problems is disclosed. The catheter has a rotating distal tip with an abrasive surface enabling the catheter to cut through and cross a CTO. The catheter includes a side cutting window and a cutting blade configured to extend through the window to cut material from the wall of a vessel at a treatment site as the catheter is pulled proximally through the treatment site. The catheter includes a material collection chamber which is positioned proximally of the cutting window. During use the rotating abrasive tip enables the catheter to cross a treatment site even if it is a CTO. The cutting window is advanced distal to the treatment site, the cutting blade is extended out the window and material is cut from the treatment site by pulling the catheter proximally across the treatment site. Since the material collection chamber is located proximal of the cutting window the length of the catheter distal to the cutting window is reduced enabling the catheter to treat lesions having short landing zones.

Although this catheter has features which overcome some of the problems described above there continues to be a need for an atherectomy catheter which can be used to access and treat lesions in the vasculature, even if the lesions are in locations which are difficult to treat with prior art catheters and even if the vessels are totally occluded at the treatment site. Further, there is need for an atherectomy catheter which is configured to efficiently transport cut debris from the location of cutting to a location of storage, even if the storage location is proximally spaced from the cutting location.

SUMMARY OF THE INVENTION

Described herein are atherectomy catheters having features which overcome the problems encountered by prior art devices. Distinguishing features that may be included in these catheters are described below. It is intended, that the catheters may include one or more at these features individually or in combination and it is not intended that the catheters be limited to the specific embodiments described herein. In one embodiment the atherectomy catheter has an inner drive shaft which rotates a distal rotary tissue borer with a helical cutting surface enabling the catheter to cut through and cross a CTO. Additionally, the atherectomy catheter has a distal cutting element rotated by an outer drive shaft configured to cut material from the all of a vessel at a treatment site as the catheter is pushed distally through the treatment site. The inner and outer drive shafts may rotate in the same direction (co-rotate) or in opposite directions (counter-rotate). The catheter includes a collection chamber positioned proximally of the cutting element and rotary tissue borer. The catheter may include means to direct material cut from the treatment site into the collection chamber. The catheters of this invention may also be optionally configured with means to break down larger portions of material that may block or clog the collection chamber and associated passageways and may be configured with means of transporting the material collected from the treatment site to a proximal opening in the atherectomy catheter.

In one variation the catheter is a material removal device for cutting material from the lumen of a vessel comprising a tubular sheath having distal and proximal ends and a lumen; a first drive shaft extending through the lumen of the tubular sheath, the first drive shaft being configured to rotate in a first direction; a second drive shaft extending through the lumen of the tubular sheath, the second drive shaft being configured to rotate in a second direction; a first cutting element coupled to the first drive shaft; a second cutting element coupled to the second drive shaft; and a driver coupled to the first and second drive shafts and configured to rotate the first drive shaft in the first direction and the second drive shaft in the second direction. The driver may comprise a single drive element coupled to both the first and second drive shafts or may optionally comprise a first drive element coupled to the first drive shaft and a second drive element coupled to the second drive shaft. The first direction of rotation may be apposite the first direction of rotation or may be the same. The first drive shaft may be rotated at a first speed of rotation and the second drive shaft may be rotated at a second speed of rotation. The first and second speeds of rotation may be the same or different. The first drive shaft may be tubular and include an inner surface which defines a lumen. The second drive shaft may be contained, at least partially, within the lumen of the first drive shaft. Optionally, a material containment chamber is defined between the outer surface of the second drive shaft and the inner surface of the first drive shaft. Optionally, at least one of the inner surface of the first drive shaft and the outer surface of the second drive shaft comprise one or more raised material transfer elements such as a rib, the one or more raised material transfer elements being configured to move material cut from the lumen of the vessel in a proximal direction. The one or more raised material transfer elements may be positioned in a helical pattern. Optionally, the first and second cutting elements have a first state in which the first and second cutting elements are contained within the lumen of the tubular sheath and a second state in which the first and second milling elements are at least partially exposed beyond the distal end of the tubular sheath.

In another variation a catheter which may include some or all of the features described above is used to cut material from lumen of a vessel at a vascular location. The method comprises advancing the tubular sheath through the lumen of the vessel to a position proximal of the vascular location; rotating the first drive shaft in a first direction within the lumen of the tubular sheath; rotating the second drive shaft in a second direction within the lumen of the tubular sheath; and with the first and second drive shafts rotating, advancing the tubular sheath distally through the lumen of the vessel across the vascular location to cut the material with the first and second cutting elements. The first and second directions may be the same or may be different. The first drive shaft may be rotated at a first, speed and the second drive shaft may be rotated at a second speed, the first speed being the same as the second speed or different from the second speed. The first drive shaft may be tubular and include an inner surface, which defines a lumen, and the second drive shaft may be contained, at least partially, within the lumen of the first drive shaft and wherein the second drive shaft is rotated within the lumen of the first drive shaft. The second drive shaft may have an outer surface, and wherein a material containment chamber is defined between the outer surface of the second drive shaft and the inner surface of the first drive shaft and wherein the method further comprises transporting the cut material proximal to the material containment chamber. At least one of the inner surface of the first drive shaft and the outer surface of the second drive shaft may comprise one or more raised material transfer elements, the one or more raised material transfer elements being configured to move material cut from the lumen of the vessel in a proximal direction, and wherein transporting the cut material proximally to the material containment chamber comprises rotating at least one of the first and second drive shafts.

These and other aspects of the invention will become apparent from the following description of the preferred embodiments, drawings and claims. The details of one or more embodiments of the invention are set forth in the accompanying drawings and the description below. Other features, objects, and advantages of the invention will be apparent from the description and drawings, and from the claims.

DETAILED DESCRIPTION

Described herein are catheters having catheter bodies adapted for intraluminal introduction to the target body lumen. The dimensions and other physical characteristics of the catheter bodies will vary significantly depending on the body lumen which is to be accessed. In the exemplary case of atherectomy catheters intended for intravascular introduction, the distal portions of the catheter bodies will typically be very flexible and suitable for introduction over a guidewire to a target site within the vasculature, n particular, catheters can be intended for "over-the-wire" introduction when a guidewire channel extends fully through the catheter body or for "rapid exchange" introduction where the guidewire channel extends of through a distal portion of the catheter body. In other cases, it may be possible to provide a fixed or integral coil tip or guidewire tip on the distal portion of the catheter or even dispense with the guidewire entirety. For convenience of illustration, guidewires will not be shown in all embodiments, but it should be appreciated that they can be incorporated into any of these embodiments which are described herein as being configured for use with a guidewire.

Catheter bodies intended for intravascular introduction will typically have a length in the range from 50 cm to 200 cm and an outer diameter in the range from 1 French to 12 French (0.33 mm: 1 French), usually from 3 French to 9 French. In the case of coronary catheters, the length is typically in the range from 125 cm to 200 cm, the diameter is preferably below 8 French, more preferably below 7 French, and most preferably in the range from 2 French to 7 French. Catheter bodies will typically be composed of an organic polymer which is fabricated by conventional extrusion techniques. Suitable polymers include polyvinylchloride, polyurethanes, polyesters, polytetrafluoroethylenes (PTFE), polyamides, silicone rubbers, natural rubbers, and the like. Optionally, the catheter body may be reinforced with braid, helical wires, coils, axial filaments, or the like, in order to increase rotational strength, column strength, toughness, pushability, kink resistance, and the like. Suitable catheter bodies may be formed by extrusion, with one or more channels being provided when desired. The catheter diameter can be modified by heat expansion and shrinkage using conventional techniques. The resulting catheters will thus be suitable for introduction to the vascular system, including both coronary arteries and peripheral arteries, by conventional techniques.

Figure 1:
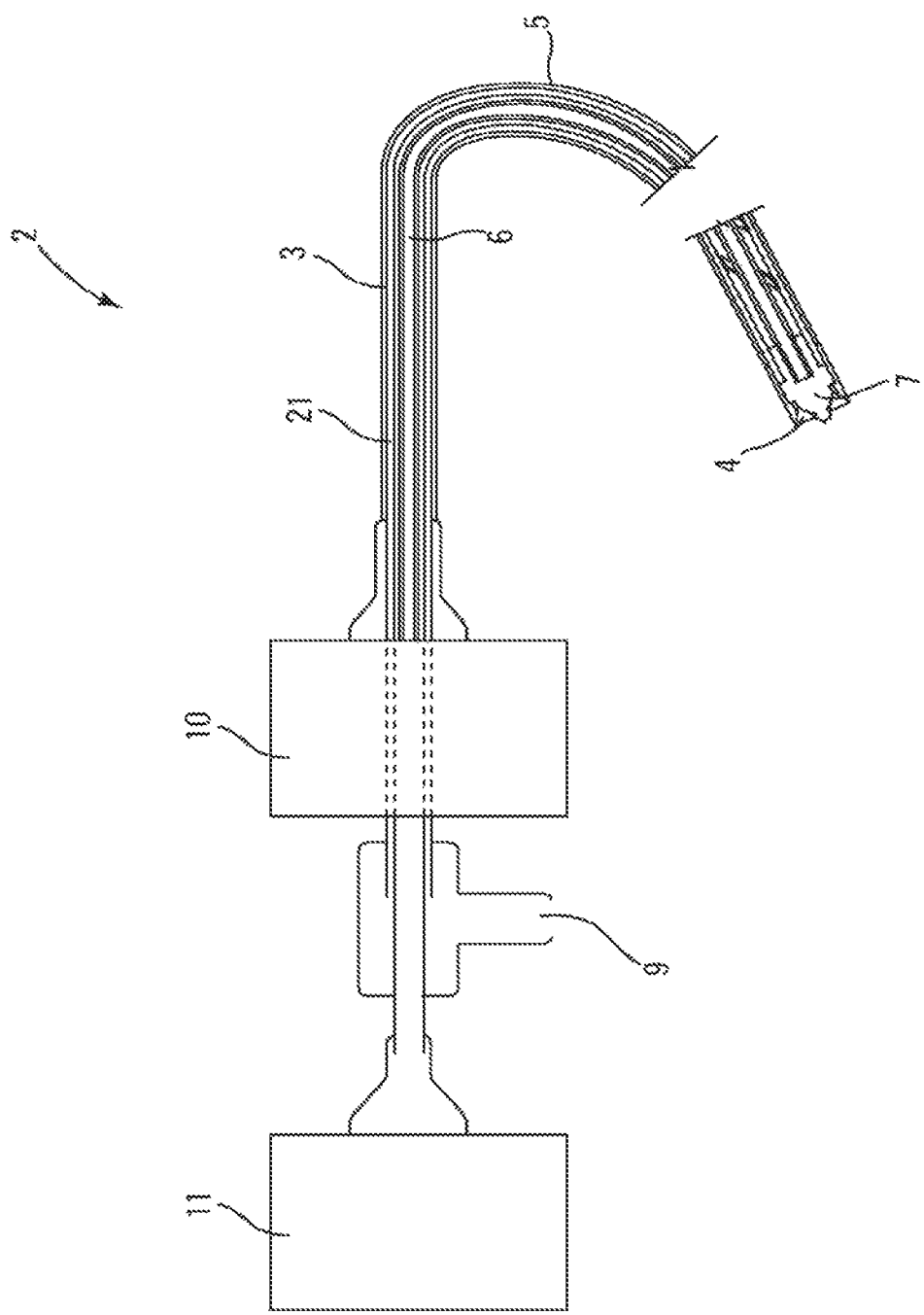
FIG. 1 illustrates a partial crabs-sectional side view of an atherectomy catheter and inner and outer cutter drivers.
Figure 2:
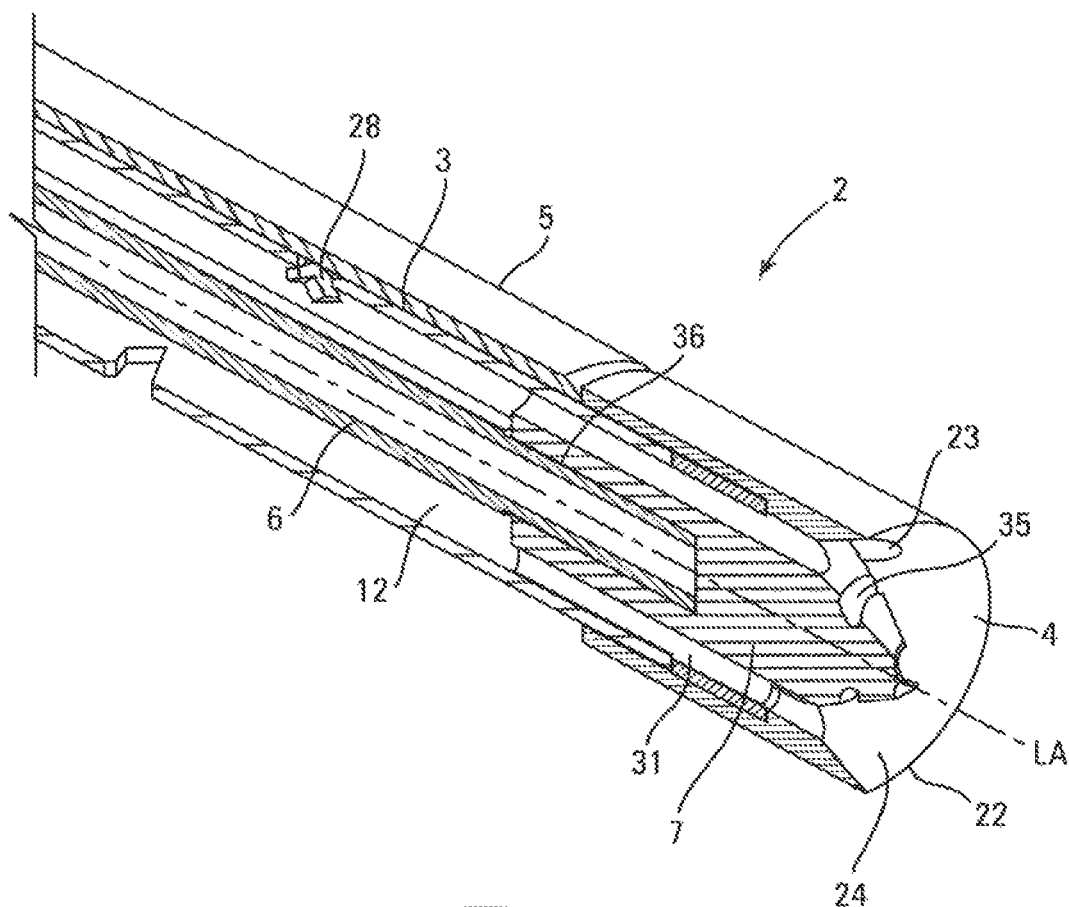
FIG. 2 illustrates a cross-sectional perspective view of a distal end portion of the atherectomy catheter of the present invention.
Figure 3:
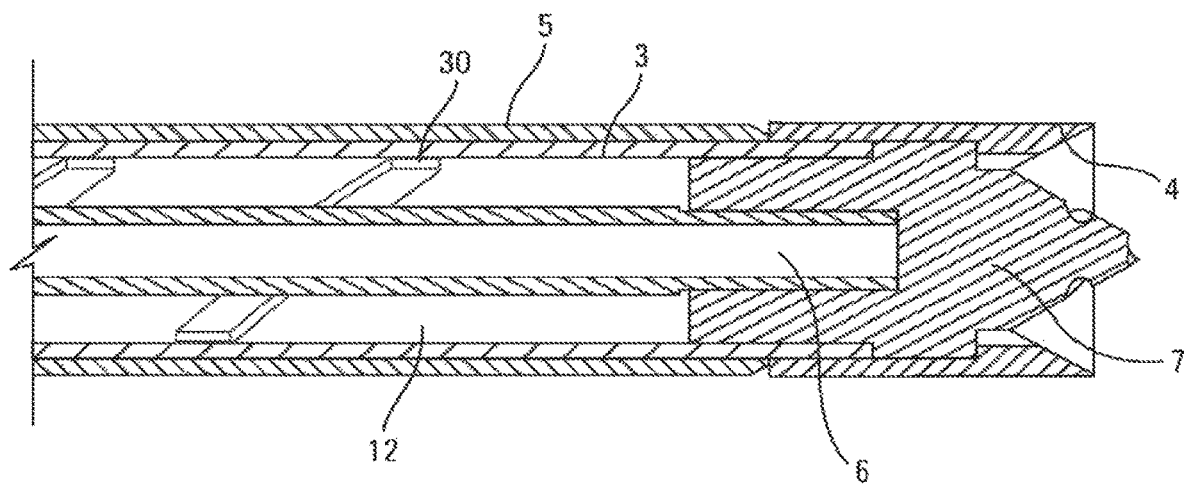
FIG. 3 illustrates a cross-sectional side view of a distal end portion of the atherectomy catheter of the present invention.

FIGS. 1 to 14 show an atherectomy catheter 2 including various optional features. As best seen in FIG. 1, which is a partial cross-sectional side view, catheter 2 has an introduction sheath 5 which is the outermost sheath or layer and is the exposed layer of the catheter to the lumen vessel. The introduction sheath 5 may be made from organic polymers and functions to aid in the transport of catheter 2 through the anatomy of a vessel. Sheath 5 may be stationary or may be configured to move longitudinally over the distal tip encapsulating the cutting tip for delivery or removal of the catheter. During use sheath 5 may be retracted to expose the cutter. Sheath 5 does not rotate when the spinning cutters are active to protect the vasculature from rotational motion of the spinning outer cutter drive shaft 3. As shown in FIGS. 2 and 3, which are cross-sectional perspective and side views, respectively, of a distal and portion of catheter 2, located directly beneath and adjacent to the introduction sheath is an outer cutter drive shaft 3 which is connected to rotate a cutting element 4 at the distal end of the catheter as discussed further below. The outer cutter drive shaft 3 may be comprised of a high modulus material or composite with flexibility and torquability e.g. a NiTi tube, stainless steel coil, or other composite layered polymer or metal material. Adequate clearance between the outer sheath 5 and the outer cutter drive shaft is provided to allow a slip fit with free rotational motion between the outer sheath and the outer cutter drive shaft. Either or both the shaft 3 and sheath 5 could be coated with a lubricious coating to reduce friction between them. Located centrally in a lumen 21 of outer cutter drive shaft 3, is inner cutter drive shaft 6. Inner cutter drive shaft 6 may be comprised of a high modulus material or composite with flexibility and torquability e.g. a NiTi tube, stainless steel coil, or other composite layered polymer or metal material. Inner cutter drive shaft 6 functions to rotate a second cutting element, more specifically a rotary tissue borer 7 which is attached to the distal end of the drive shaft 6.

Figure 4:
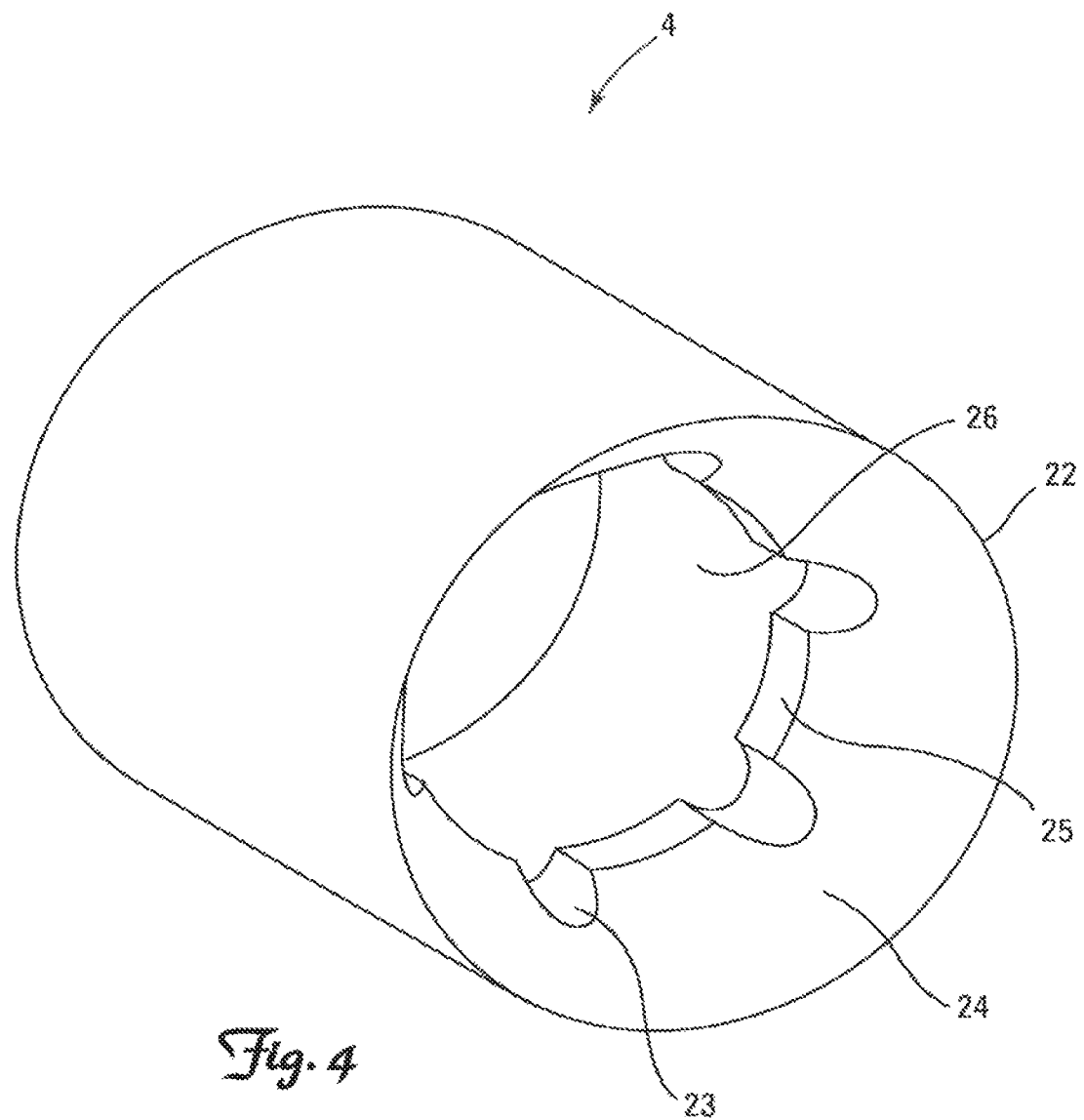
FIG. 4 illustrates a perspective view of a distal cutting Element of the atherectomy catheter of the present invention.

Distal cutting element 4 is shown in more detail in FIG. 4. Distal cutting element 4 is attached to outer cutter drive shaft 3 by welding, soldering, adhesive and the like. Distal cutting element 4 is used to cut material from a blood flow lumen such as are arterial or venous blood vessel and transport tissue material collected from the distal tip of the catheter towards a proximal opening and is discussed in greater detail below. Catheter 2 includes rotary tissue borer 7 (the second of the two cutting elements), attached to inner cutter drive shaft 6 by welding, soldering, adhesive and the like. Rotary tissue borer 7 may be used to bore through any occlusion in a lumen that may otherwise prevent distal movement of the catheter through the vessel and may aid in the transport of tissue material collected from the distal tip of the catheter through distal openings or flutes and towards a proximal opening 9 and is discussed in greater detail below.

Outer cutter drive shaft 3 of catheter 2 is coupled at its proximal end to an outer cutter driver 10 which rotates the outer drive shaft 3 and also the attached distal cutting element 4. Inner cutter drive shaft 6, which extends through lumen 21 of outer cutter drive shaft 3, is coupled at its proximal end to inner cutter driver 11 which rotates the inner drive shaft 6 and also the attached rotary tissue borer 7. The outer cutter driver 10 and inner cutter driver 11 separately power and rotate the inner cutter drive shaft and the outer cutter drive shaft allowing each drive shaft to rotate clockwise or counter-clockwise. In one embodiment catheter 2 may be used with both the inner cutter drive shaft 6 and the outer cutter drive shaft 3 rotating clockwise or both counter-clockwise. In another embodiment one of the inner and outer cutter drive shafts may rotate clockwise and the other of the inner and outer cutter drive shafts may rotate counter-clockwise. The inner and outer cutter drive shafts may be rotated at the same speed or at different speeds as discussed in more detail hereafter. Although not shown, it will be understood by those of skill in the art that through the use of appropriate gearing a single drive motor could be used to rotate both the inner cutter drive shaft and the outer cutter drive shafts.

Catheter 2 is comprised of a tissue collection chamber 12. Tissue collection chamber 12 comprises the annular space between the inner surface of the outer cutter drive shaft and the outer surface of the inner cutter drive shaft and extends substantially the entire length of the catheter between the cutting elements and the handle, as shown in FIGS. 2 and 3, for example. Catheter 2 may be provided with proximal opening 9 with tubing attached thereto to facilitate suction of cut debris or injection of fluid (including medications) through the annular space between the outer cutter drive shaft 3 and the inner cutter drive shaft 6.

Outer cutter driver 10 and inner cutter driver 11 are substantially similar and may include any suitable drive motor and power source (for example, one or more batteries) as known in the art. Cutter drivers 10 and 11 are incorporated into a handle which can be attached at the proximal end of the catheter. The handle will include one or more levers or switches to control the motors. In one embodiment both cutters drivers would be switched on together, rotating in opposite directions. Alternatively, each driver may have a control switch so that each may be energized independently of the other. Thus it is possible to rotate either cutter independently of the other and potentially with different speed or rotational direction. This is advantageous in situations where it is desired to rotate only the inner cutter while leaving the outer cutter stationary, for example for tissue transportation through the tissue collection chamber 12 without continuing to cut with the outer cutting element 4. Additionally, after crossing a CTO it is advantageous to retract the inner cutter and continue to cut atheroma with the outer cutter. Thus, the inner cutter drive shaft may be longitudinally moveable with respect to the outer cutter drive shaft. Longitudinal advancement or retraction of the inner cutter drive shaft is controlled by a control lever on the handle. In another embodiment there is one switch which is used to energize both cutter drivers simultaneously. The control handle could be provided with controls giving the operator the ability to control the direction of rotation of each of the cutters.

Distal cutting element 4 is rotated about a longitudinal axis LA of catheter 2 when the outer cutter drive shaft 3 rotates. Distal cutting element 4 may be rotated at about 1 to 160,000 rpm but may be rotated at any other suitable speed depending upon the particular application. The cutting element 4 may be formed of one continuous part or may be comprised of multiple parts subsequently joined together by welding, soldering, brazing, adhesive bonding, mechanical interlock or other means. Cutting element 4 may be formed from any suitable material capable of holding a cutting edge with abrasion resistance, for example, hardened steel, carbide or Ti-nitride coated steel. As shown in FIG. 4, distal cutting element 4 may have a cup-shaped surface 24, which directs the tissue cut by the cutting edge 22 through openings or cutting element flutes 23 and into tissue chamber 12. Cutting element 4 includes a distal cutting edge 22 positioned at a radially outer circumferential edge of distal cutting element 4. During use, as cutting element 4 is rotated, cutting edge 22 makes a generally circular cut into the material to be removed. Cup shaped surface 24 directs the cut material radially inward.

Flutes 23, in combination with the rotation of the helical grooves 35 of rotary tissue borer 7, act to break down the material. The flutes have a semi-cylindrical shape oriented generally parallel with the longitudinal axis (alternatively, the flutes could be oriented at a angle with respect to the longitudinal axis) of the catheter and have a diameter of between 0.001 and 0.030 inches, more typically between 0.008 and 0.010 inches and have a length of between 1 and 10 mm, more typically between 4 to 6 mm. The size of the flutes is selected to allow a sufficient space for the cut material to enter the annular collection chamber located between the inner and outer cutter drive shafts.

The force applied to the catheter against the lesion facilitates the cut material to enter the catheter through these openings during use. Cutting element 4 includes a substantially cylindrical interior surface which steps down in diameter at a borer ledge 25. A proximately oriented annular surface lying within a plane generally perpendicular to the longitudinal axis of the catheter connects reduced diameter borer ledge 25 to the larger diameter portion of the interior surface. Ledge 25 has an inner circumference slightly larger than that of the rotary tissue borer 7 but smaller than the circumference of the outer cutter drive and functions as a bearing surface which allows rotation but which limits the distal movement of rotary tissue borer 7. This prevents rotary tissue borer 7 from being extended beyond the distal end of catheter 2 more than a desired distance. The outer cutter drive shaft may be connected at a proximal location 26 of the distal cutting element by welding, soldering, brazing, or adhesive bonding.

Figure 5:
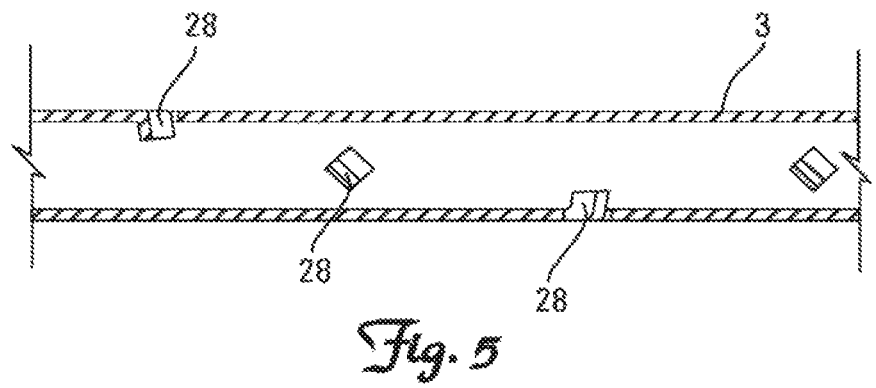
FIG. 5 illustrates a side cross-sectional view of one embodiment of an outer cutter drive shaft of the atherectomy catheter of the present invention.
Figure 6:
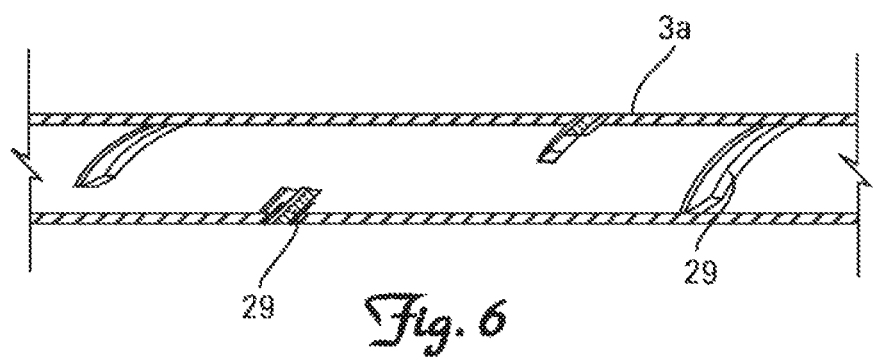
FIG. 6 illustrates a side cross-sectional view of another embodiment of an outer cutter drive shaft of the atherectomy catheter of the present invention.
Figure 7:
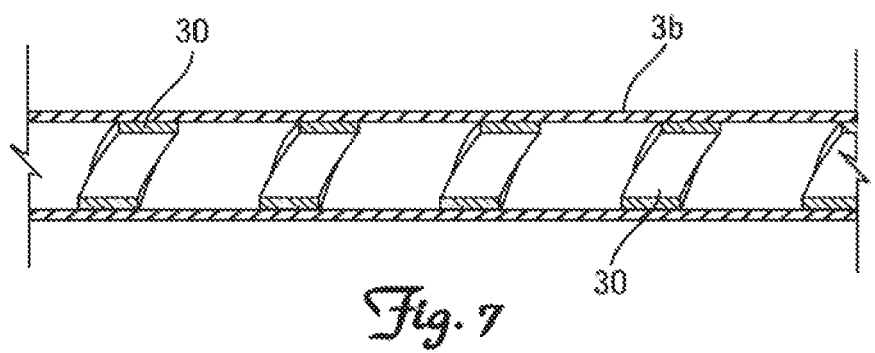
FIG. 7 illustrates a side cross-sectional view of yet another embodiment of an outer cutter drive shaft of the atherectomy catheter of the present invention.

Cross-sectional side views of different embodiments of outer cutter drive shaft 3 are shown in FIGS. 5 to 7, In the embodiment of FIG. 5, outer cutter drive shaft 3 has push-down shears 28 which are notched into the surface of the outer cutter drive shaft when it is formed and then pushed in towards the inner diameter of the outer cutter drive shaft. The shears are formed by laser or by mechanically cutting a partial outline of the profile of the shears into the outer cutter drive shaft. After being cut the shears are pushed inwardly. Push-down shears 28 are discontinuous and may follow a helical winding pattern that may be spaced at any distance from each other depending upon the application. Shears 28 are provided for at least a portion or all of outer cutter drive shaft 3 between the handle and the cutters. Additionally, a laminate could be added to the outer surface of drive shaft create a water/air tight seal, for example, a polyester heat shrink.

In another embodiment as shown in FIG. 6, outer cutter drive shaft 3a has push-down discontinuous helical rib 29 which is formed substantially similar to that of push down shears 28. The outline of helical rib 29 is notched Into the outer surface of the outer cutter drive shaft when is formed and then pushed down towards the inner diameter of the outer drive shaft. Helical rib 29 is formed so that each discontinuous portion of the rib is spaced a sufficient distance from adjacent portions to ensure the structural integrity of the drive shaft. The discontinuous portions are provided for at least a portion or ail of the drive shaft and may follow a helical winding pattern. Additionally a laminate could be added to the drive shaft 3 to create a water/air tight seal for example a polyester heat shrink tube.

In another embodiment as shown in FIG. 7, outer cutter drive shaft 3b has helical rib 30 which is continuous and follows a helical winding pattern for at least a portion or all of the outer drive shaft. Helical rib 30 is formed onto the inner diameter of outer cutter drive shaft 3. The helical could be formed by attaching a tube to the inner surface of outer cutter drive shaft 3, the tube having a helix attached to the inside wall of the tube, or the tube being a molded tube with an infernal helix. It should be noted that helical rib 30 of the outer cutter drive shaft may be formed discontinuous as in push down shears 28 or may have separate continuous helical winding patterns spaced a predetermined distance apart down the length of the tissue chamber depending upon the application. Shears 28, and helical ribs 29 and 30 may direct tissue towards the proximal opening 9 and also break down clots that may have formed or larger portions of tissue material collected. The outer cutter drive shaft may be made from any suitable material having sufficient flexibility. It should be noted that the outer cutter drive shaft may be formed without the shears or helical ribs depending upon the application or a combination of both. Further, the slope of the helical pattern of the shears and ribs could be selected in accordance with the particular application to which the catheter is to be used. It should also be noted that the outer cutter drive shaft 3 (or the outer cutter drive shafts of any of the other embodiments disclosed herein) could be additionally coated with a lubricant, Teflon, or other coating to reduce atheroma/tissue from sticking to the outer cutter drive shaft, or with an anticoagulant or thrombolytic coating such as heparin or urokinase to prevent blood coagulation within tissue collection chamber 12.

Figure 8:
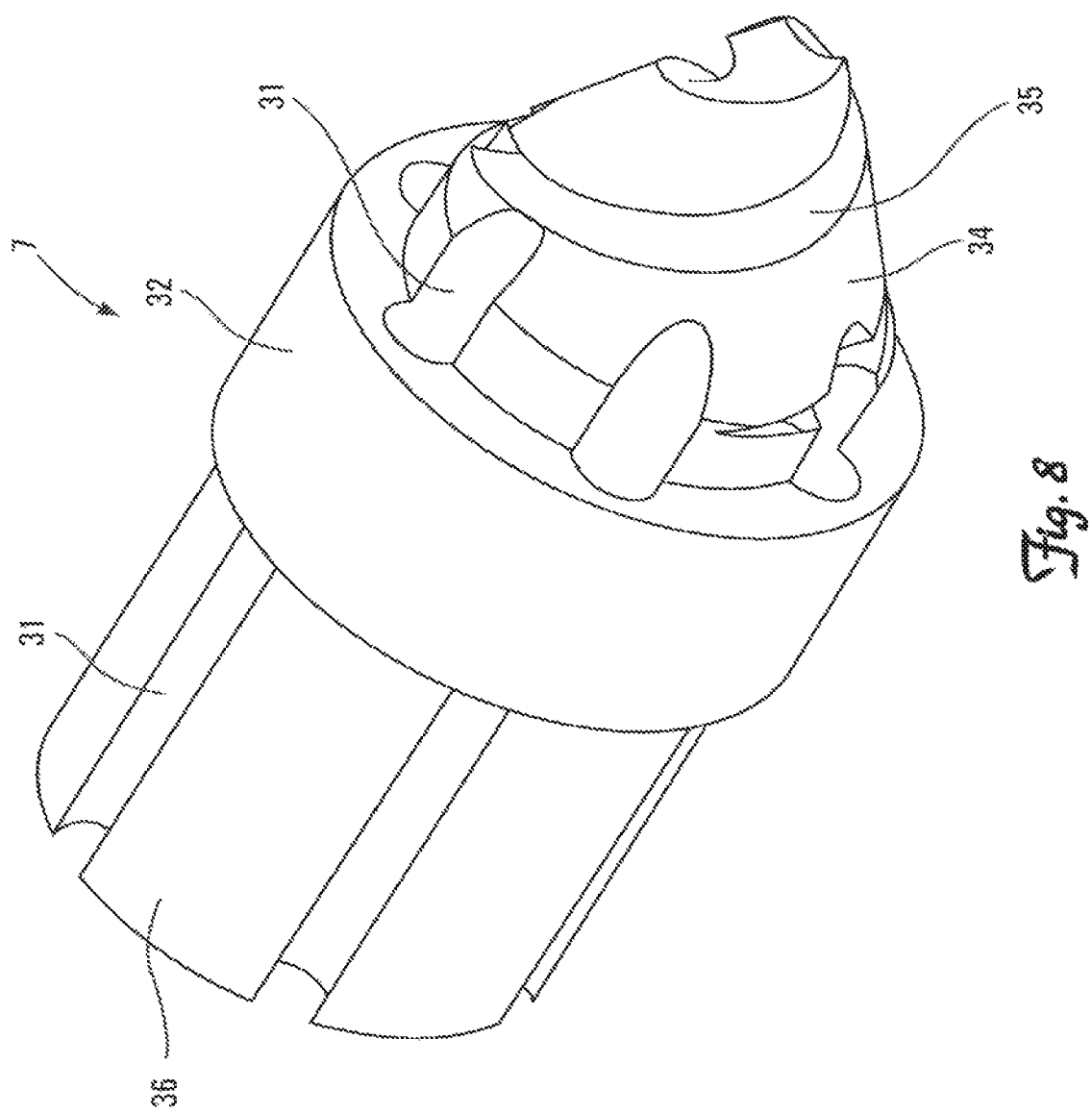
FIG. 8 illustrates a perspective view a rotary tissue borer of the atherectomy catheter of the present invention.

Rotary tissue borer 7 is rotated about a longitudinal axis LA of the catheter as the inner cutter drive shaft rotates. The rotary tissue borer 7 is rotated about 1 to 160,000 rpm but may be rotated at any other suitable speed depending upon the particular application. The rotary tissue borer may be formed of one continuous part or may be comprised of multiple parts subsequently joined together by welding, soldering, brazing, adhesive bonding, mechanical interlock or other means. As shown in FIG. 8, rotary tissue borer 7 has distal portion 34 which can be formed with a helical cutting surface 35 and can bore through occlusions in a lumen and direct the tissue cut by the tissue borer through openings or borer flutes 31 (and cutter element flutes and into tissue chamber 12. Tissue borer 7 is sized to fit within distal cutting element 4. More specifically, tissue borer 7 includes a bushing 32 at the base of distal portion 34. Bushing 32 has a circumferential outer surface which is larger than the distal portion 34 of the rotary tissue borer 7 but smaller than the circumferential inner surface of the ledge 25 of outer cutter drive shaft 3. Bushing 32 includes a distally oriented annular surface which is sized to abut against the proximately oriented annular surface of ledge 25 and functions as a bearing to allow rotation while limiting the distal movement of the rotary tissue borer 7. Borer flutes 31 extend from a proximal portion 36 through to distal portion 34. Flutes 31 and flutes 23 are provided with a shape that allows cut debris to move proximally into the collection chamber. For example, flutes 31 may have a semi-cylindrical cross sectional shape along the surface of the proximal and distal portions and a cylindrical shape as they extend through the bushing 32. The diameter of flutes 31 may be the same as flutes 23. Flutes 31 provide a dual function. First, they function in combination with flutes 23 to shear material cut by the cutting edge of the outer cutter and by the tissue borer and, second, they allow the material which is cut to pass through the distal end of the catheter and into the tissue collection chamber of catheter 2. Proximal portion 36 accepts the distal end of inner cutter drive shaft 6 as can be seen in FIGS. 2 and 3 and may be affixed by welding, soldering, brazing, or adhesive bonding.

Figure 9:
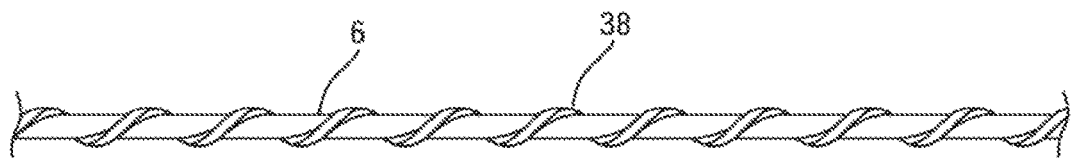
FIG. 9 illustrates a side view of one embodiment of an inner cutter drive shaft of the present invention.
Figure 10:
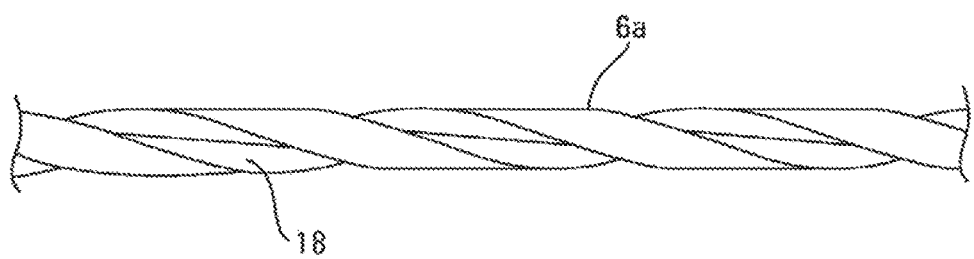
FIG. 10 illustrates a side view of another embodiment of an inner cuter drive shaft of the present invention.
Figure 11:
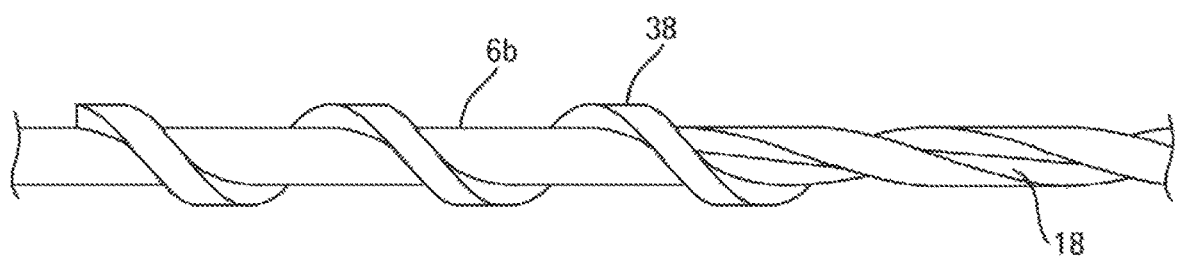
FIG. 11 illustrates a side view of yet another embodiment of an inner cutter drive shaft of the present invention.
Figure 12:
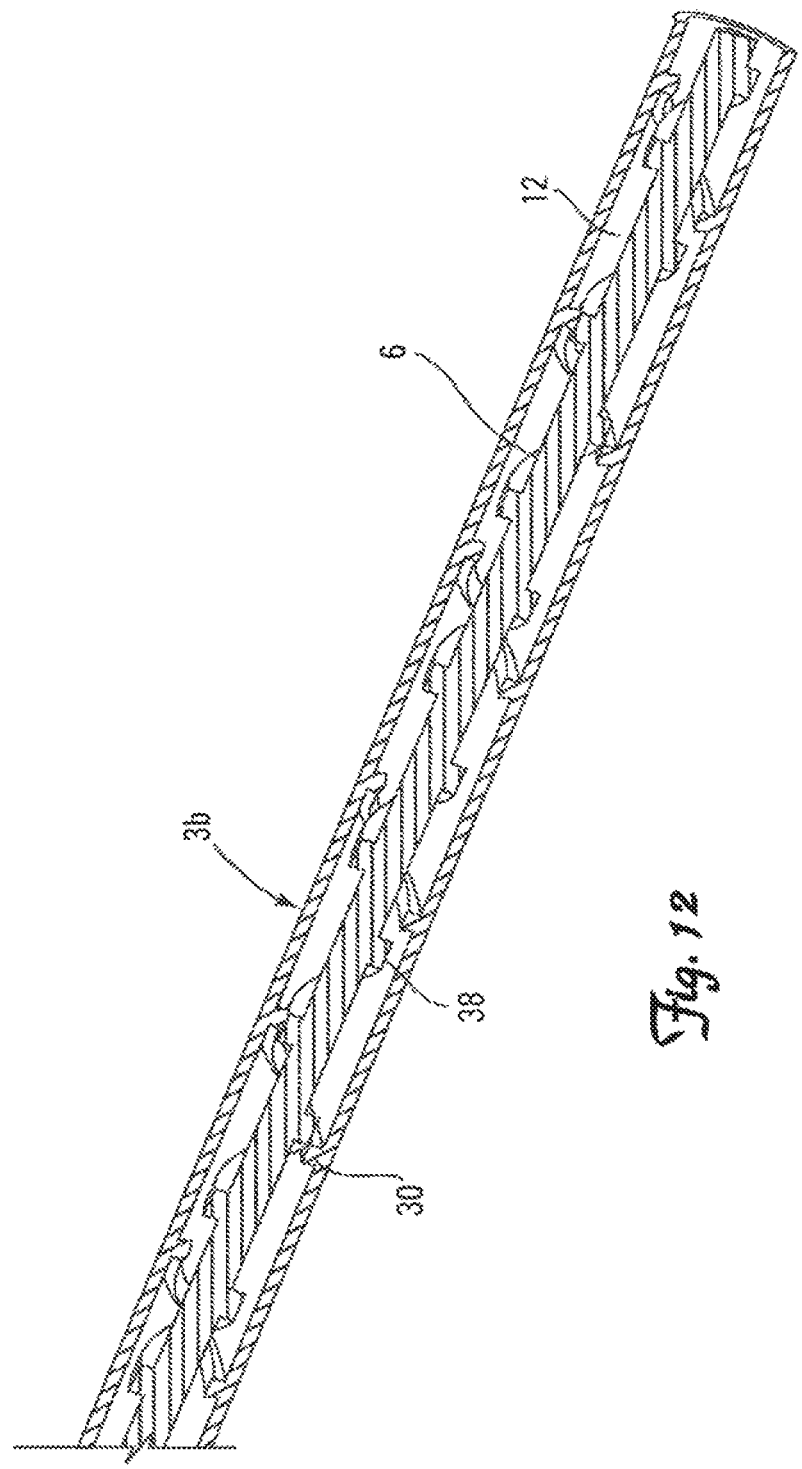
FIG. 12 illustrates cross-sectional perspective side view of a tissue chamber of the atherectomy catheter of the present invention.

Views of multiple embodiments of inner cutter drive shaft 6 are shown separated from the rest of the catheter 2 in FIGS. 9 to 11. Inner cutter drive shaft 6 may be made from any suitable material having sufficient flexibility and may be substantially solid or hollow depending upon the application. Suitable materials include high modulus materials or composites with flexibility and torquability, e.g., a NiTi tube, stainless steel coil, or other composite layered polymer or metal material. In some applications, where the inner cutter drive shaft is hollow, a guidewire lumen 37 may run the length of the inner cutter drive shaft. The inner cutter drive shaft may be made of helically wound stainless steel wires that may be left hand or right hand wound and that have welded proximal and distal ends that do not extend past the outside dimension of the wound wires. The inner cutter drive shaft may be made of braided steel wires. In some embodiments, the inner cutter drive shaft may be comprised of multiple layers of helically wound wires. In some cases adjacent layers of helical wound wires are wound with opposite handedness.

A partial view of an inner cutter drive shaft 6 is shown in FIG. 9. The inner cutter drive shaft is oriented in FIG. 9 such that the proximal and distal ends of the drive shaft (not shown) would lie to the left and right sides of FIG. 9, respectively. Inner cutter drive shaft 6 has been formed with a left handed helical winding 38 that is for at least a portion or all of the drive shaft as desired. The helix may be wound as a left handed winding pattern as shown in FIG. 9 or with a right handed helical winding pattern as shown in FIGS. 10 and 11. In either case, the helix would be rotated in a direction so as to draw material proximally. As the inner cutter drive shaft 6 rotates in a counter-clockwise direction the helical winding 38 rotates, and cut material collected through bore flutes 31 and cutter element flutes 23 at the distal end of the catheter 2 is directed towards proximal opening 9 (from right to left in FIG. 9). Additionally, as both the inner and outer cutter drive shafts rotate in opposite directions, the physical and compressive forces created by the counter-rotation of the helical windings 38 of the inner drive shaft 6 and the shears 28 or helical ribs of the outer drive shaft, break down blood clots that may have formed and larger portions of tissue collected. Of course, as explained in more detail hereafter, the inner and outer cutter drive shafts may be counter-rotated at the same or different speeds or they may be rotated in the same direction at the same or different speeds.

Inner cutter drive shaft 6a of FIG. 10 has been formed with helical channel 18. Helical channel 18 may be formed in the surface of a solid or hollow shaft by a laser or mechanical cutting process. This process results in the formation of a helical rib between the channel 18 that function in a manner similar to drive shaft 6 of FIG. 9.

Inner cutter drive shaft 6*b* of FIG. 11 combines features of both drive shafts 6 and 6*a*. Drive shaft 6*b* has been formed with a portion having helical windings 38 and a portion having helical channel 18. It should be noted that the helical windings of the inner cutter drive shaft may be made discontinuous as in the shape and spacing of the push down shears 28 of the outer cutter drive or may have separate continuous helical winding patterns spaced a predetermined distance apart down the length of the tissue chamber depending upon the application. Helical windings 38 and helical channel 18 may direct tissue towards the proximal opening 9 and also break down clots that may have formed or larger portions of tissue material collected. The inner cutter drive shaft may be made from any suitable material having sufficient flexibility. It should be noted that the inner cutter drive shaft may be formed without the helical windings or the helical channel depending upon the application or may be made with any combination of both and further; the helical pattern of the shears and ribs could be linear or any suitable pattern. It should also be noted that the inner cutter drive shaft 6 (or the inner cutter drive shafts of any of the other embodiments disclosed herein) could be additionally coated with a lubricant such as Teflon, or other coating to reduce atheroma/tissue from sticking to the inner cutter drive shaft, or with an anticoagulant or thrombolytic coating such as heparin or urokinase to prevent blood coagulation within tissue collection chamber 12.

During an exemplary use of the catheter, the catheter is advanced through the vessel until the distal end of catheter 2 along with the distal cutting element 4 and rotary tissue borer 7 are positioned adjacent or just proximal to the proximal end of a treatment site of a vessel. Once the distal cutting element 4 and the rotary tissue borer 7 have been moved to the proper longitudinal position within the vessel, outer cutter driver 10 is engaged to rotate the outer cutter drive shaft and distal cutting element counter-clockwise. The inner cutter driver 11 is also engaged to rotate the inner cutter drive shaft and rotary tissue borer clockwise. It should be noted that the rotation for the inner drive shaft could be rotating counter-clockwise while the outer cutter drive shaft is rotating clockwise, or both cutter drive shafts could be rotating clockwise or counter-clockwise depending on the direction of orientation of the helical ribs. The directions of rotation and the orientation of the helical ribs (left handed or right handed) will be selected so that the net result is to cause the cut material to be transported through the catheter in a proximal direction from the distal end of the catheter towards the proximal end. This may be accomplished if both the inner and outer cutter drive shafts are designed to propel material in a proximal direction. It can also be accomplished if one of the inner and outer drive shafts is designed to move material proximally and one is designed to move material or fluid distally, so long as the one that moves material proximally provides a greater propelling force or, in other words, a greater transfer rate. For example, the inner cutter drive shaft may have a helical rib orientation and a direction of rotation that moves material proximally while the cuter cutter drive shaft has a rib or shear orientation and direction of rotation that tends to propel material distally. So long as the propelling force provided by the inner cutter drive shaft is greater than that provided by the outer cutter drive shaft (provided by a faster speed of rotation or a larger winding pitch with larger capacity of material) the direction of travel of material through the catheter will be proximal. Alternatively, the outer cutter drive shaft may have a rib or shear orientation and direction of rotation that moves material proximally while the inner cutter drive shaft has a helical rib orientation that Lends to propel material or fluid distally. So long as the propelling force provided by the outer cutter drive shaft is greater than that provided by the inner cutter drive shaft the direction of travel of material through the catheter will be proximal. In these embodiments the opposing propelling forces may even act to further break down the material to make it easier to transport. It should further be noted that one of the cutter drive shafts may be rotating while the other is stationary depending upon the application. It should be further noted that the two cutter drive shafts, and thus the distal cutting element and rotary tissue borer attached thereto can rotate at the same speed or at different speeds depending upon the application.

After the cutter driver or drivers have been energized the catheter 2 is pushed distally through the vessel with the distal cutting element 4 and the rotary tissue borer 7 in the rotating or cutting position as described in further detail below, it should be noted that in some applications, only the rotary tissue borer 7 may be engaged to rotate in order to safely bore through a total occlusion. As the catheter 2 moves distally through the blood vessel, the tissue material cut by the distal cutting element 4 and rotary tissue borer is directed by cup shaped surface 24 into the cutter element flutes 23 and borer flutes 31 and through to the tissue collection chamber 12 positioned proximal to the distal cutting element 4 and rotary tissue borer 7. As can seen in FIG. 12, tissue collection chamber 12 has the outer cutter drive shaft with helical ribs 30 following a continuous helical right winding pattern through the chamber and inner cutter drive shaft 6 has helical windings 38 following a continuous helical left winding pattern through the chamber. The rotation of the helical windings 38 create a force as the inner cutter drive shaft 6 is engaged which can direct the tissue collected in the tissue collection chamber towards proximal opening 9 when drive shaft 6 is rotated in a counter-clockwise direction. Additionally or alternatively, the rotation of the helical ribs 30 can also create a force as the outer cutter drive shaft is engaged which can also direct the tissue collected in the tissue collection chamber toward the proximal opening when the outer cutter drive shaft is rotated in a clockwise direction. The left or right winding orientation of the helical ribs and the helical windings in combination with the clockwise or counter-clockwise rotation of the inner and outer cutter drives can aid in the direction of flow of material through the tissue chamber and can vary depending upon the application. It should be noted that the slant, size, left or right winding patterns and spacing of the helical windings, helical channels, helical ribs and shears of the present invention can all vary depending upon the application and the desired material transfer rate.

Figure 13:
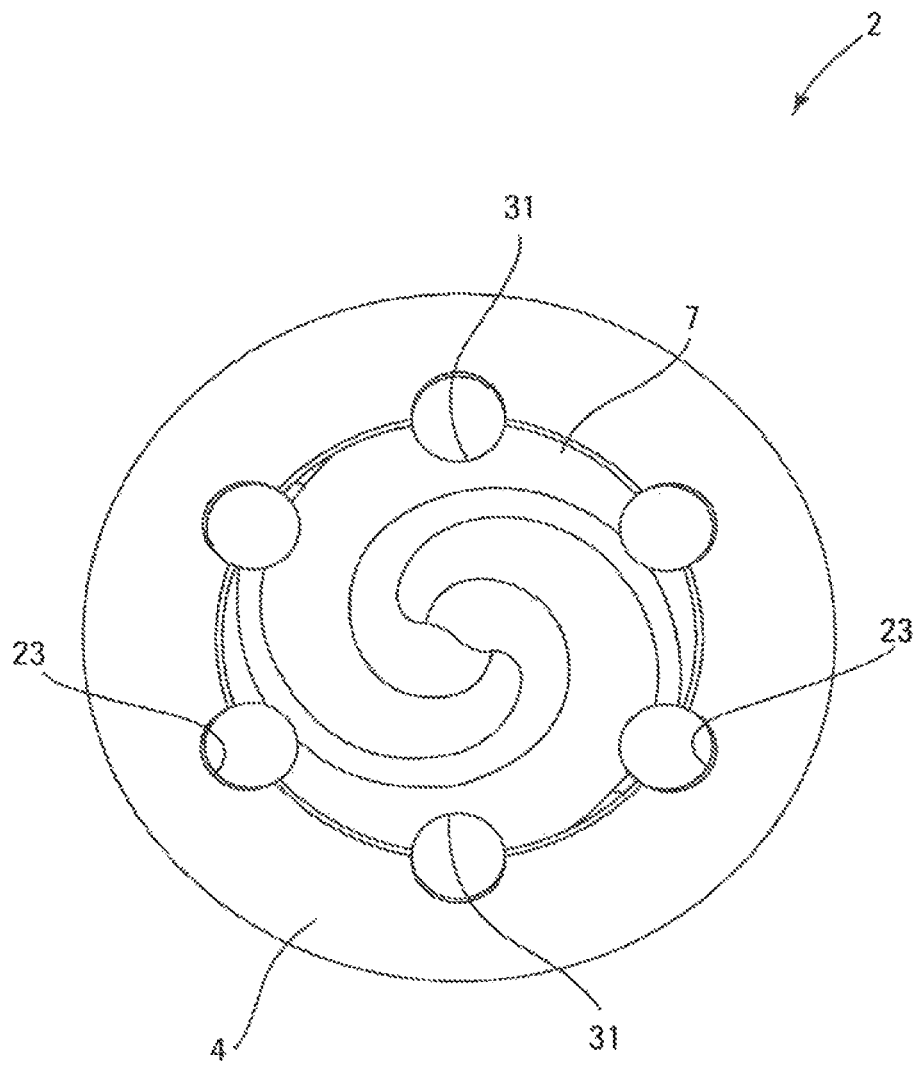
FIG. 13 illustrates a distal end view of alignment of cutter element flutes and borer flutes of the atherectomy catheter of the present invention.
Figure 14:
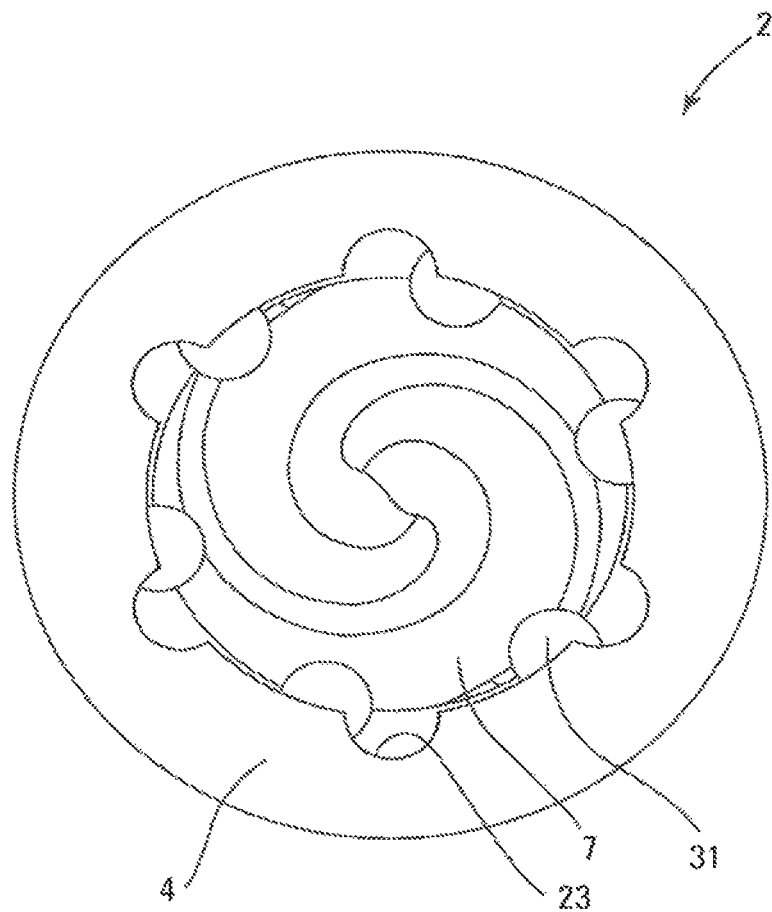
FIG. 14 illustrates a distal end view of non-alignment of cutter element flutes and borer flutes of the atherectomy catheter of the present invention.

FIGS. 13 and 14 illustrate a distal end view of catheter 2. In FIG. 13 the cutter element flutes 23 of the distal cutting element 4 and the borer flutes 31 of the rotary tissue borer 7 are aligned and create a circular chute or passage through which material cut from the lumen of a vessel can pass in order to enter the annular collection chamber. FIG. 14 illustrates that as the distal cutting element 4 and the rotary tissue borer 7 counter-rotate (or co-rotate at different speeds) the continuous off-setting and realigning of the flutes causes the shearing down of the material collected as it passes through borer flutes 31 and cutter element flutes 23. It should be noted that the shearing of the tissue as the borer flutes and cutting element flutes off set and realign can also be caused by the same directional rotation of both the rotary tissue borer and distal cutting element at different speeds. This shearing effect created by the counter rotating of the tissue borer and cutting element breaks down larger tissue material allowing easier passage of the collected tissue through the flutes and into the tissue collection chamber.

The tissue is sheared and directed through the flutes of the distal cutting element and rotary tissue borer and into tissue collection chamber 12. The material collection chamber is elongated to accommodate the material which has been cut and may be as long as the catheter length. The proximal portion of the catheter body may additionally have proximal opening 9 so tissue transported through the catheter can exit through the opening or sidewall port. Since the tissue collection chamber is positioned proximal of the cutting element and tissue borer as length is not constrained by the size of the landing zone of the treatment site, the tissue collection chamber can be made to have any desired length. The rotation of the helical windings 38 or helical channels 19 can create a force as the inner cutter drive shaft 6 is engaged which can direct the tissue collected in the tissue collection chamber proximally towards proximal opening 9 depending upon the direction of the rotation of the helical windings or helical channels. Additionally or alternatively, the rotation of the push down shears 28 (or helical ribs 29 and 30) can create a centripetal force as the outer cutter drive shaft is engaged which can direct the material collected in the tissue collection chamber inwardly toward the inner drive shaft 6a depending upon the direction of rotation of the push down shears (or helical ribs 29 and 30). The forces created by the movement and momentum of the rotation of the helical windings on the inner cutter drive shaft causes the cut material and blood clots to further break down and degrade as they encounter the centripetal force created by the movement and momentum of the rotation of the push down shears 28 of the outer cutter drive shaft 3. These forces of the helical windings/and or push down shears may also create suction through the borer flutes 31 of the rotary tissue borer 7 and cutter element flutes 23 of distal cutting element 4, aiding in the passage of material through the flutes. It should be noted that additional suction may be applied in some applications as desired through proximal opening 9 to aid in the collection of material.

In a further example of use, catheter 2 cuts softer atheroma from a vessel wall in relatively large strips and cup shaped surface 24 of distal cutting element 4, along with rotary tissue borer 7 in some applications, directs these strips through cutter element flutes 23 and borer flutes 31 and into collection chamber 12. Since collection chamber 12 is positioned proximal of both the rotary tissue borer and distal cutting element 4 it is desirable to keep the cutter element flutes 23 and borer flutes 31 as free from obstruction as possible, for example, from strips of tissue that are too large to pass through the flutes of the tissue borer and the cutting element. The counter rotation of the rotary tissue borer 7 and the distal cutting element 4, or in some applications the differing speeds of same directional rotation, create a shearing force as the cutter element flutes 23 and borer flutes 31 align and non-align that help to break down larger strips of tissue and allow for easier transport of the tissue through the flutes and into the tissue collection chamber.

It is further desirable to keep the tissue collection chamber as free from obstruction as possible to allow the proximal movement of the tissue collected towards proximal opening 9. Another potential obstruction can occur where tissue collected in the tissue collection chamber has clotted or occluded, hindering the movement of cut material from the collection chamber towards the proximal opening. As explained above, the forces created by the movement and momentum of the rotation of the helical windings, helical ribs, helical channels and push down shears cause any occlusion or clotting to break into smaller fragments in response to shear forces created by the movement and momentum of the rotation of the push down shears 28 of the outer cutter drive shaft 3. The rotation of the inner cutter drive shaft and outer cutter drive shaft may be counter-rotational or same direction rotational, depending upon the application. It may be further desirable to keep constant advancement of collected tissue in the tissue collection chamber from the distal end of the catheter towards the proximal opening. As explained above, the rotation of the helical windings 38 can create a force as the inner cutter drive shaft 6 is engaged which can direct the tissue collected in the tissue collection chamber towards proximal opening 9 depending upon the direction of the rotation of the helical windings. Additionally or alternatively, the rotation of the push down shears 28 can also create a centripetal force as the outer cutter drive shaft is engaged which can also direct the tissue collected in the tissue collection chamber toward the proximal opening depending upon the direction of rotation of the push down shears. In some applications, both the inner cutter drive shaft and outer cutter drive shaft can have the same proximal directional rotation. In other applications, the inner cutter drive shaft and the outer cutter drive shaft may have counter-directional rotation. In the applications where the forces created by one of the drive shafts transports material or fluid distally and the forces created by the other of the drive shafts transports material proximally, the speed of rotation, rib size and/or pitch of the ribs or push down shears of the drive shaft which transports material proximally, may have to be greater than the speed of rotation, rib size and/or pitch of the ribs or push down shears of the drive shaft which transports material distally, so that the force created by the drive shaft causing proximal transport of material will overcome the opposing force created by the other drive shaft. Thus, the drive shaft should be designed and operated in a manner which results in a net force which moves material proximally. Rib size, clearance between shears and drive shaft, pitch, relative rotational speed between the rotating shafts, and surface finish or frictional coefficient of the interfacing members can affect tissue transporting ability and may be designed to maximize the efficiency of desired tissue transport.

Figure 15:
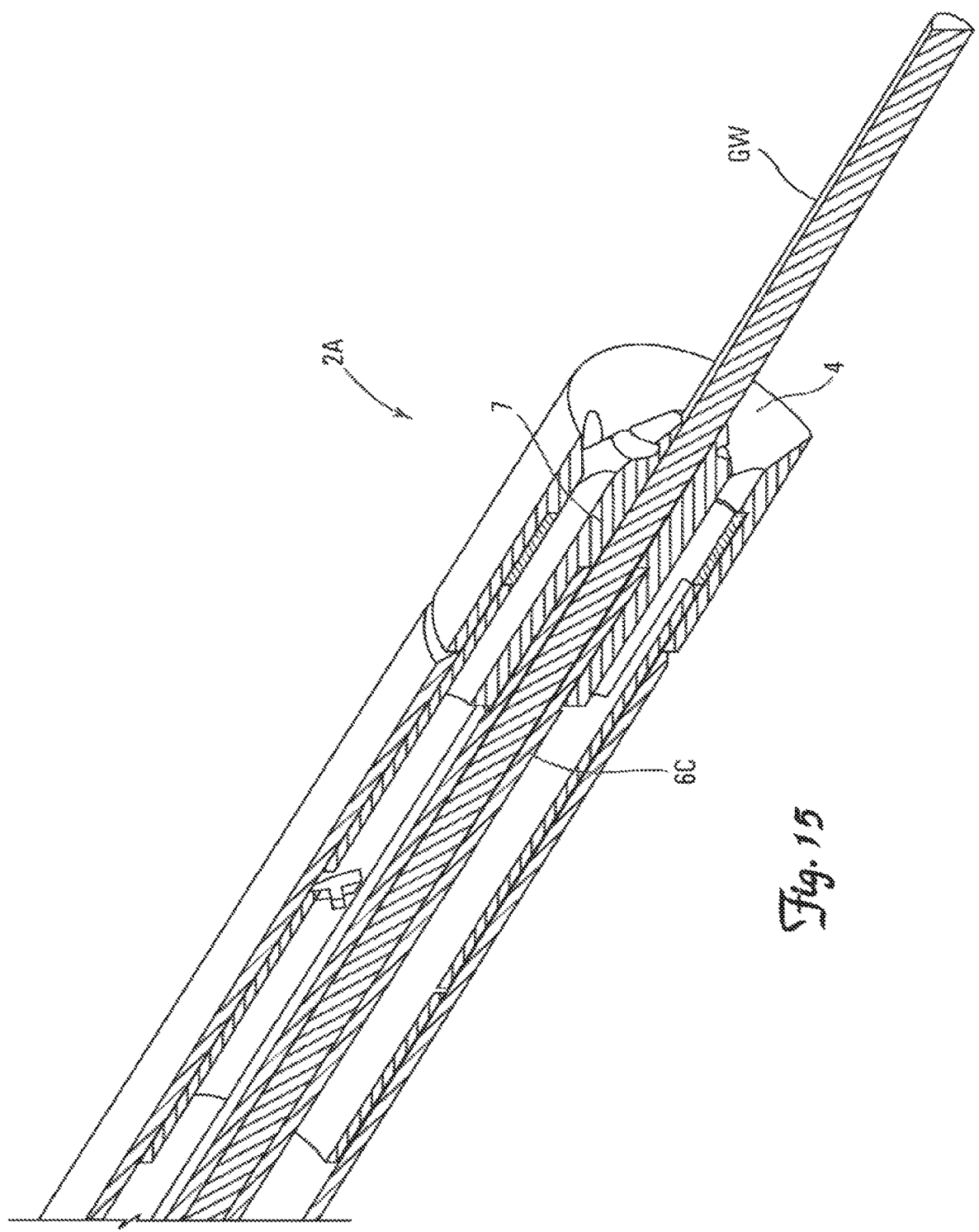
FIG. 15 illustrates a cross sectional perspective of an alternate embodiment of the atherectomy catheter of the present invention.
Figure 16:
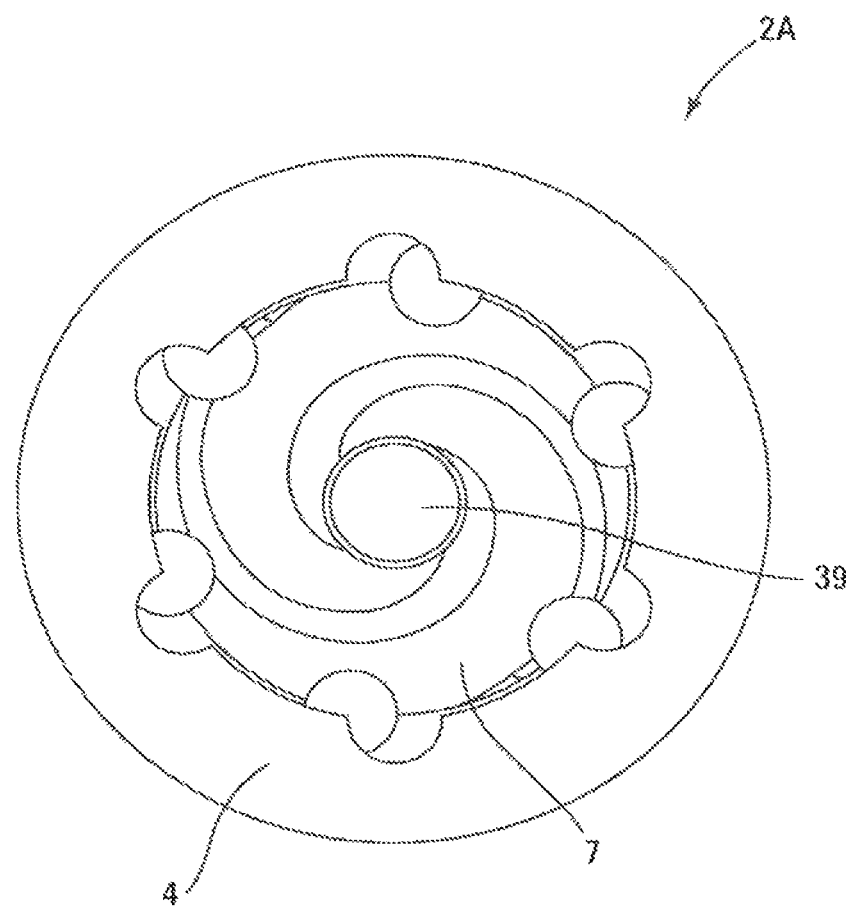
FIG. 16 illustrates an end view of the atherectomy catheter of FIG. 15.

FIGS. 15 to 18 are views of alternate embodiments of the catheter of FIGS. 1 to 14. Catheter 2A is shown wherein the same or similar reference numbers of catheter 2A refer to the same or similar structures of catheter 2 and all discussion concerning the same or similar features of catheter 2 are equally applicable here unless noted otherwise. In a first embodiment shown in FIGS. 15 and 16, inner cutter drive shaft 6c of catheter 2A is hollow and has guidewire lumen 37 that runs the entire length of the inner cutter drive shaft. Guidewire lumen 39 of rotary tissue borer 7 is positioned to align with guidewire lumen 37 of the inner cutter drive 6c. The guidewire lumens of the inner cutter drive shaft and the rotary tissue borer extend from the proximal end to the distal end of catheter 2A so that the catheter may be used as an over-the-wire catheter. FIG. 15 shows catheter 2A with a guidewire GW.

Figure 17:
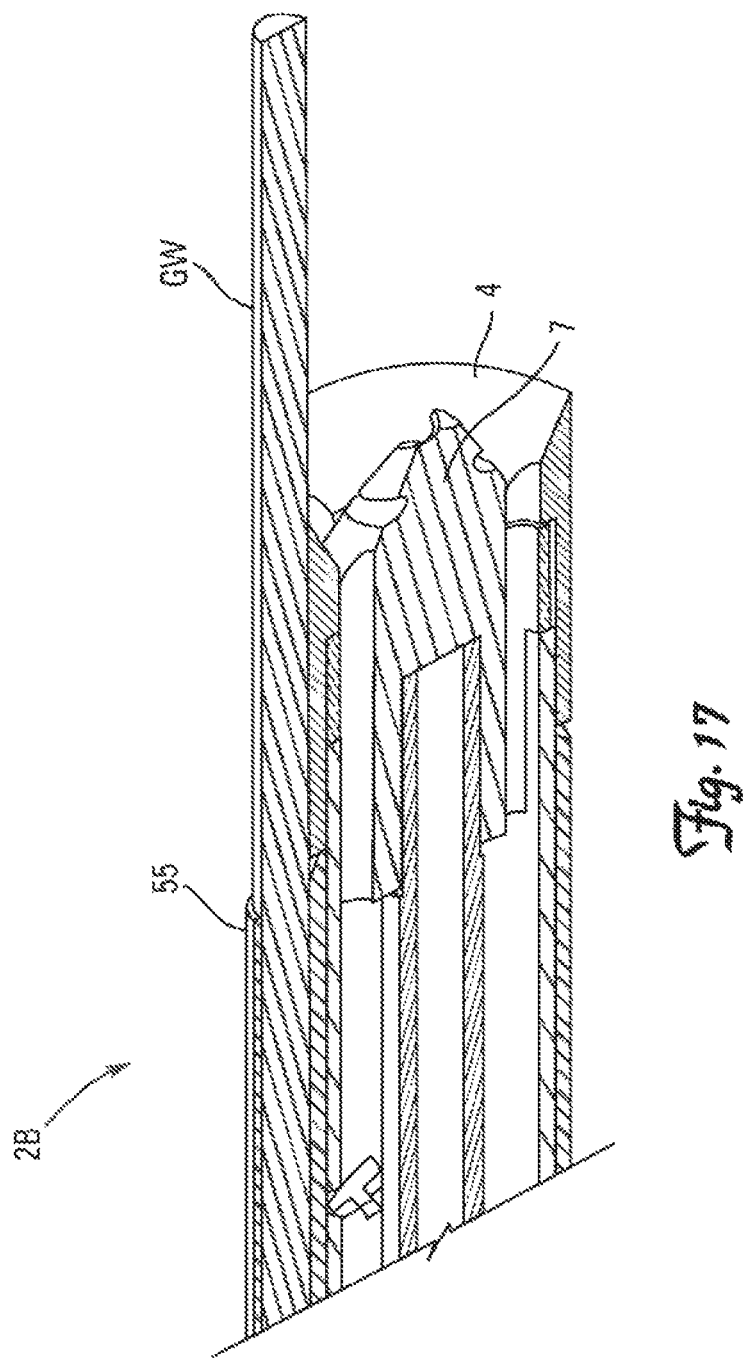
FIG. 17 illustrates a cross sectional perspective of an alternate embodiment of the atherectomy catheter of the present invention.
Figure 18:
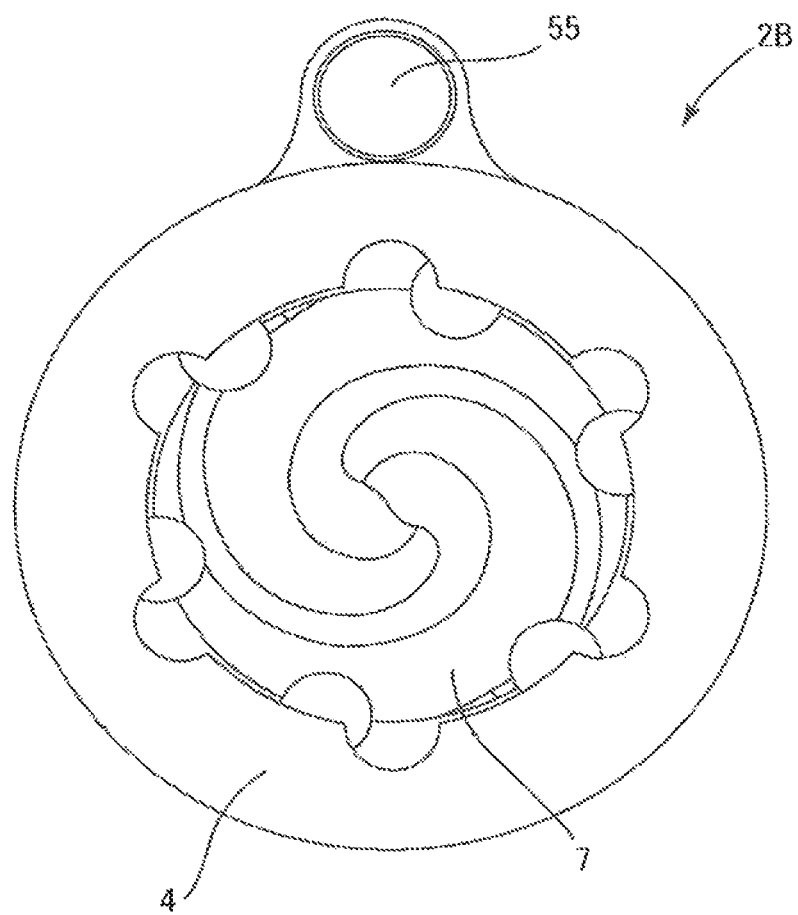
FIG. 18 illustrates an end view of the atherectomy catheter of FIG. 17.

FIGS. 17 and 18 show an embodiment of the invention comprising a rapid exchange catheter. Catheter 2B is shown wherein the same or similar reference numbers of catheter 2B refer to the same or similar structures of catheter 2 and all discussion concerning the same or similar features of catheter 2 are equally applicable here unless noted otherwise. Catheter 2B includes a side mounted tubular portion 55 which forms a relatively short guidewire lumen for receipt of a guidewire GW. Side mounted tubular portion 55 may be 1 to 30 cm long depending upon the application.

Figure 19A:
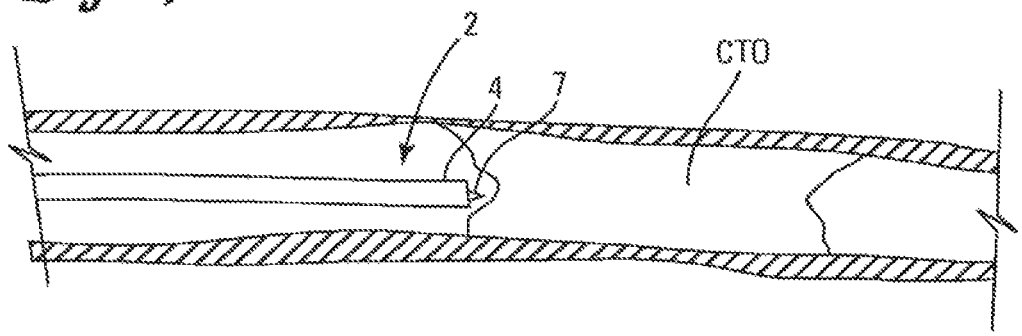
FIG. 19A is an illustration of a first position of an atherectomy catheter during a method of using the atherectomy catheter.
Figure 19B:
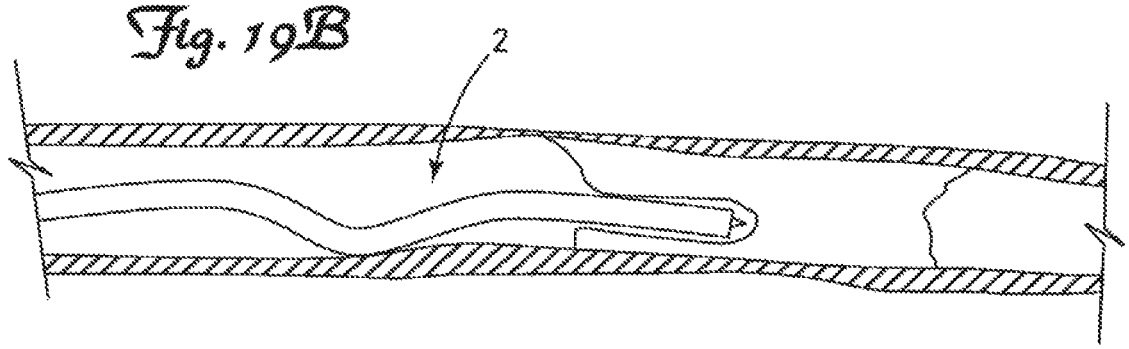
FIG. 19B is an illustration of a second position of an atherectomy catheter during the method.
Figure 19C:
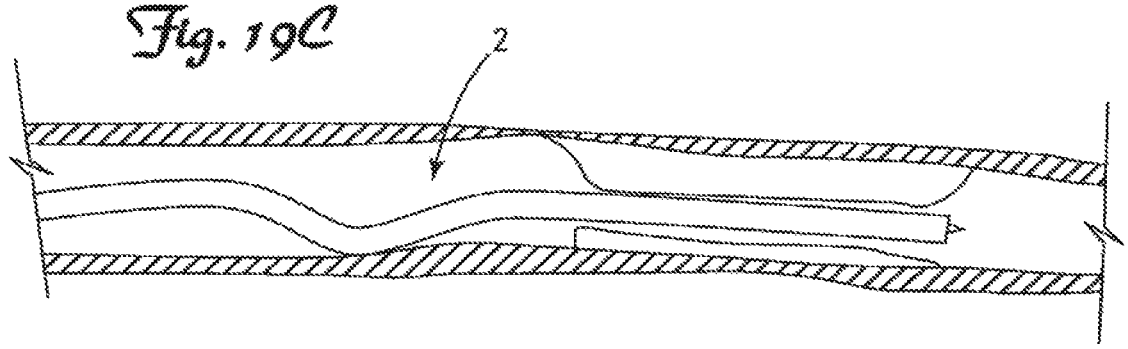
FIG. 19C is an illustration of a third position of an atherectomy catheter during the method.

Exemplary methods of using the catheters of FIGS. 1 to 18 are hereby described and shown in FIGS. 19A to 19C. A guidewire is percutaneously introduced into a patient's body and advanced to a region of interest in a patients blood vessel V. If the treatment site is a CTO, as shown in FIG. 19A, the guidewire may be unable to cross the lesion. FIG. 19A illustrates a totally occluded lumen in which a guidewire (GW) has been advanced to the proximal side of the occlusion. Catheter 2 has been advanced over the guidewire to a position just proximal of the occlusion. In FIG. 19A the guidewire is not shown since it has been withdrawn into the catheter. During advancement the distal cutting element and the rotary tissue borer are in their stationary positions and may be covered by sheath 5. A traditional prior art catheter would either have to be forced across the lesion or treatment would have to be abandoned in favor of another form of treatment. With catheter 2 (and the other catheters described herein) the occlusion may e safely crossed by energizing one or both of outer cutter driver 10 and inner cutter driver 11 to rotate the inner and outer cutter drive shafts. Rotation of the inner cutter drive shaft causes the rotary tissue borer 7 to rotate. The rotary tissue borer 7 cuts through even calcified material enabling the catheter to be slowly advanced through the lesion while the distal cutting element 4 also engages the treatment site to cut material from the lesion as shown in FIGS. 19B and C. It should be noted that in some applications only the inner center drive may be engaged to rotate the rotary tissue borer so as to initially bore through a total occlusion; in other applications it may be necessary to initially only engage the outer cutter drive and rotate the distal cutting element at a treatment site. The cut material is directed through the cutting element flutes and the borer flutes and into the collection chamber. Force applied to catheter 2 and against material M causes a pressure that helps to force cut material through flutes 23, 31. This cutting process can be repeated by advancing and retracting the catheter across the treatment site until a sufficient amount of material has been removed. At any time during the procedure, debris may be suctioned through the catheter or fluid may be introduced to the vessel through the catheter through the annular space between the inner and outer drive shafts. Additionally, at any time during the procedure the guidewire may be removed and debris may be suctioned through the guidewire lumen or fluid may be introduced to the vessel through the guidewire lumen. Catheter 2B, shown in FIGS. 17 and 18, is used as described above except that it is advanced to the treatment site over a guidewire positioned in the guidewire lumen defined by side mounted tubular portion 55.

Figure 20:
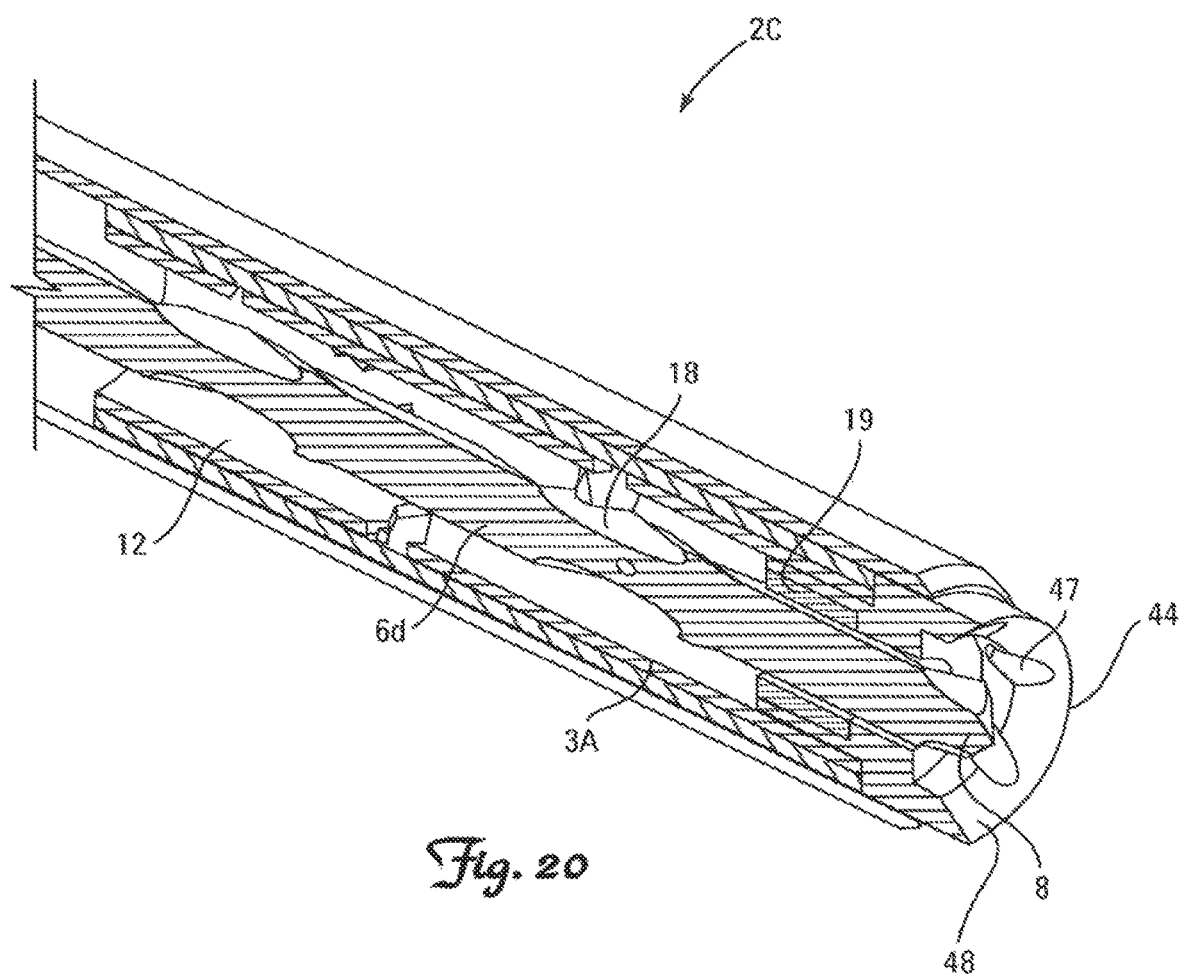
FIG. 20 is a cross sectional perspective of another embodiment of the atherectomy catheter of the present invention.
Figure 21:
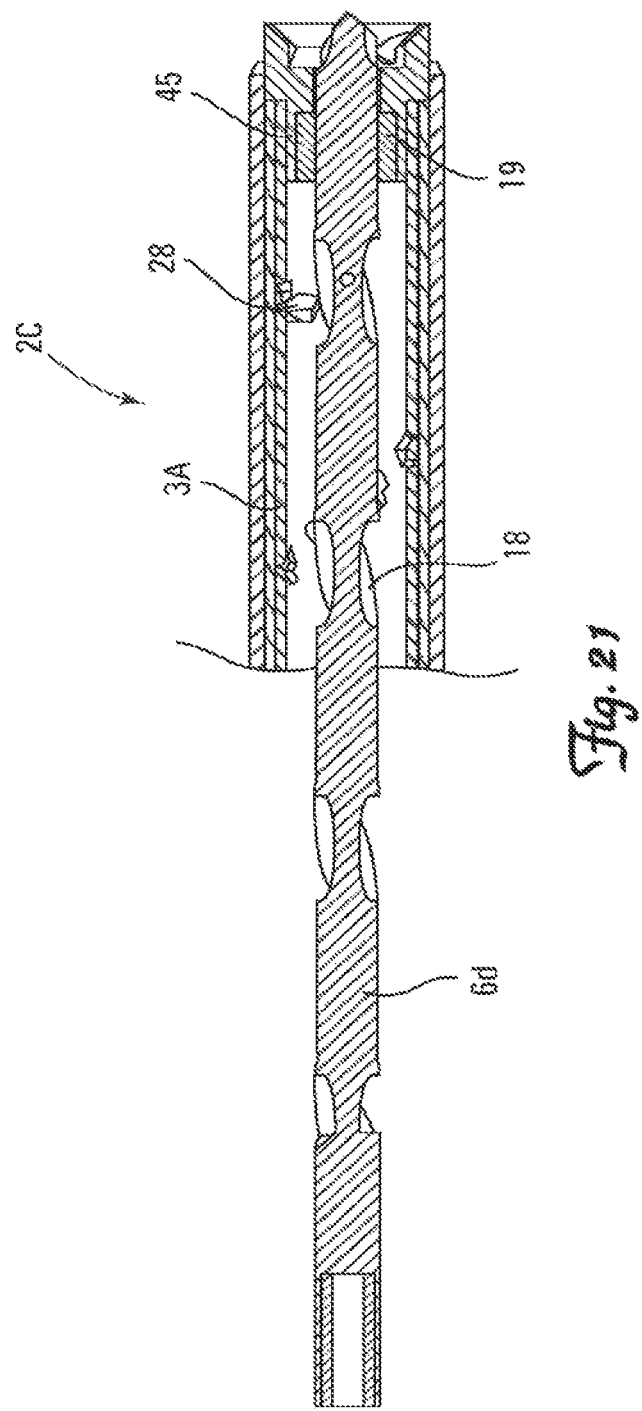
FIG. 21 is a side view of the atherectomy catheter of FIG. 20.
Figure 22:
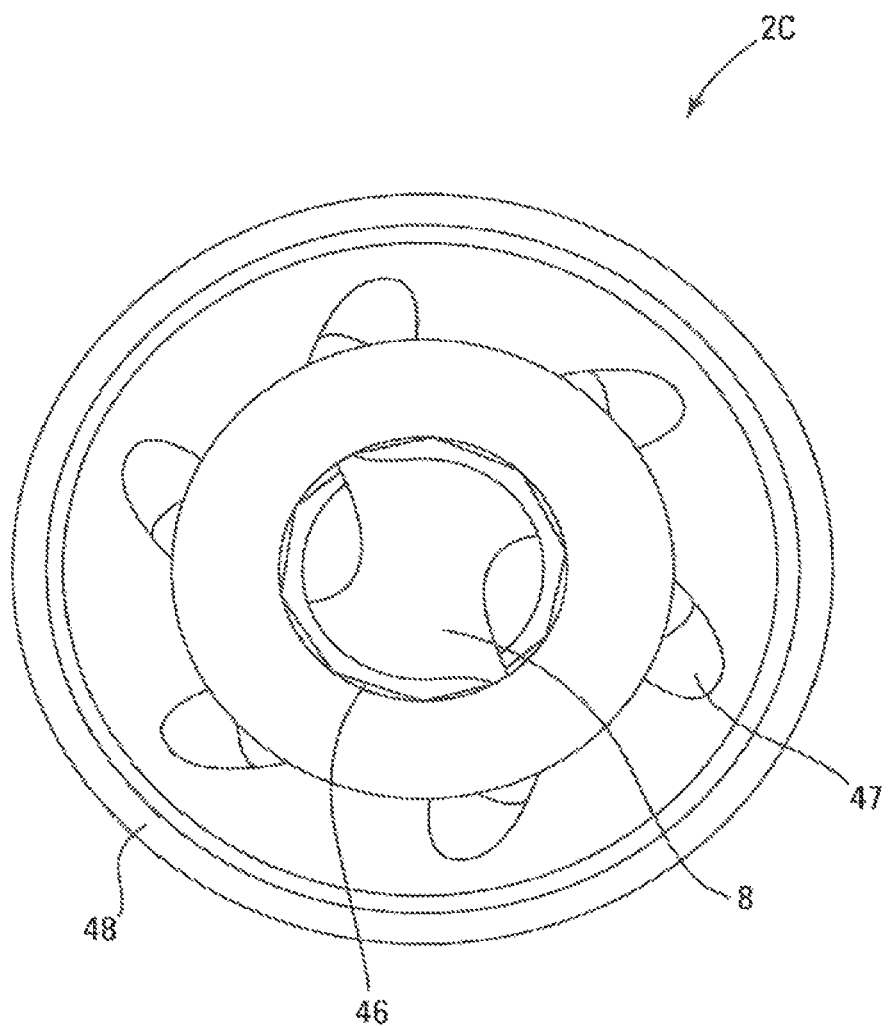
FIG. 22 is a distal end view of the atherectomy catheter of FIG. 20.

An alternative catheter embodiment is shown in FIGS. 20 to 22. Catheter 2C is shown wherein the same or similar reference numbers of catheter 2C refer to the same or similar structures of catheter 2 and all discussion concerning the same or similar features of catheter 2 are equally applicable here unless noted otherwise. Compared to catheter 2, inner cutter drive shaft 6d does not have a separate rotary tissue borer. Inner cutter drive shaft 6a has been formed with a borer tip 8 which can bore through occlusions in a lumen. Inner cutter drive shaft 6d has been additionally formed with helical channels 18 which transport material cut by borer tip 8 and by distal cutting element 44 into tissue chamber 12 through helical flutes 47 in distal cutting element 44. Distal cutting element 44 includes a central opening 46 which has an inner circumference slightly larger than the outer circumference of inner cutter drive shaft 6d. As the inner cutter drive shaft 6d rotates, the depression of the helical channels 18 cause material to be transported from the distal end of the catheter through drive shaft bushing 19 and into collection chamber 12. Inner cutter drive shaft has attached drive shaft bushing 19 which can be formed, welded, soldered and the like onto the surface of the inner cutter drive shaft 6d and is housed in cutting element portion 45 which has an inner circumference slightly larger than that of the outer circumference of drive shaft bushing 19 and which functions as a bearing to allow rotation of the inner drive shaft but to limit the distal movement of inner cutter drive shaft 6d. Cutting element flutes 47 direct cut material or tissue inwardly towards the inner cutter to thus allow the tissue to pass through the grooves 18 at the distal end of the catheter and into the tissue collection chamber of catheter 2. In some embodiments, distal cutting element 44 may have a cup-shaped surface 48 which may be a smooth and continuous surface free of through holes, teeth, fins or other features, which disrupt the smooth nature of the surface 48; in other embodiments the cup shaped surface may have a limited amount of teeth, fins or other features. The outer cutter drive shaft 3a may be connected to the distal cutting element 44 at cutting element portion 45 by welding, soldering, brazing, or adhesive bonding. This connection allows cutting element 44 to rotate as outer cutter drive shaft 3a rotates.

Figure 23:
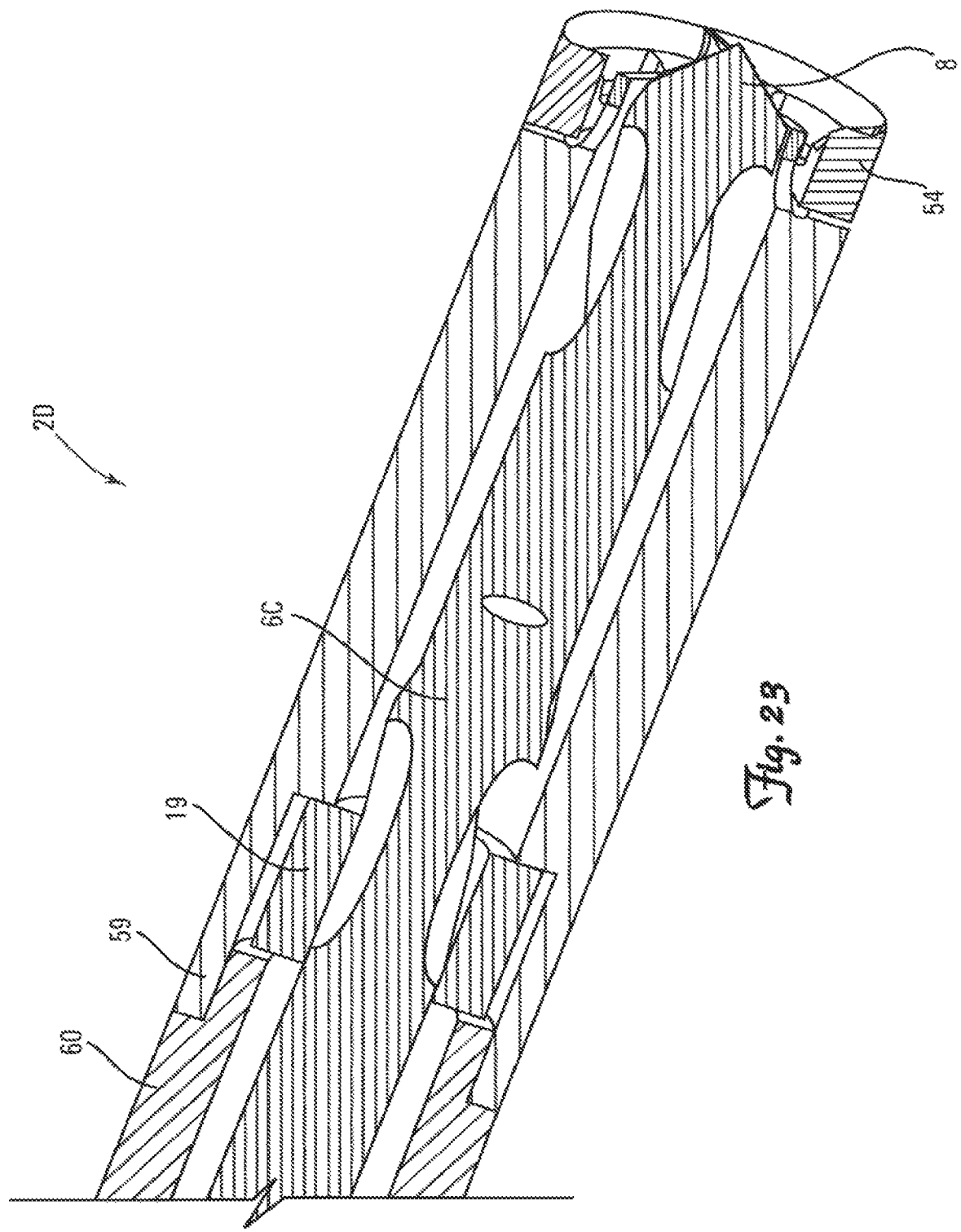
FIG. 23 is a cross sectional perspective of another embodiment of the atherectomy catheter of the present invention.
Figure 24:
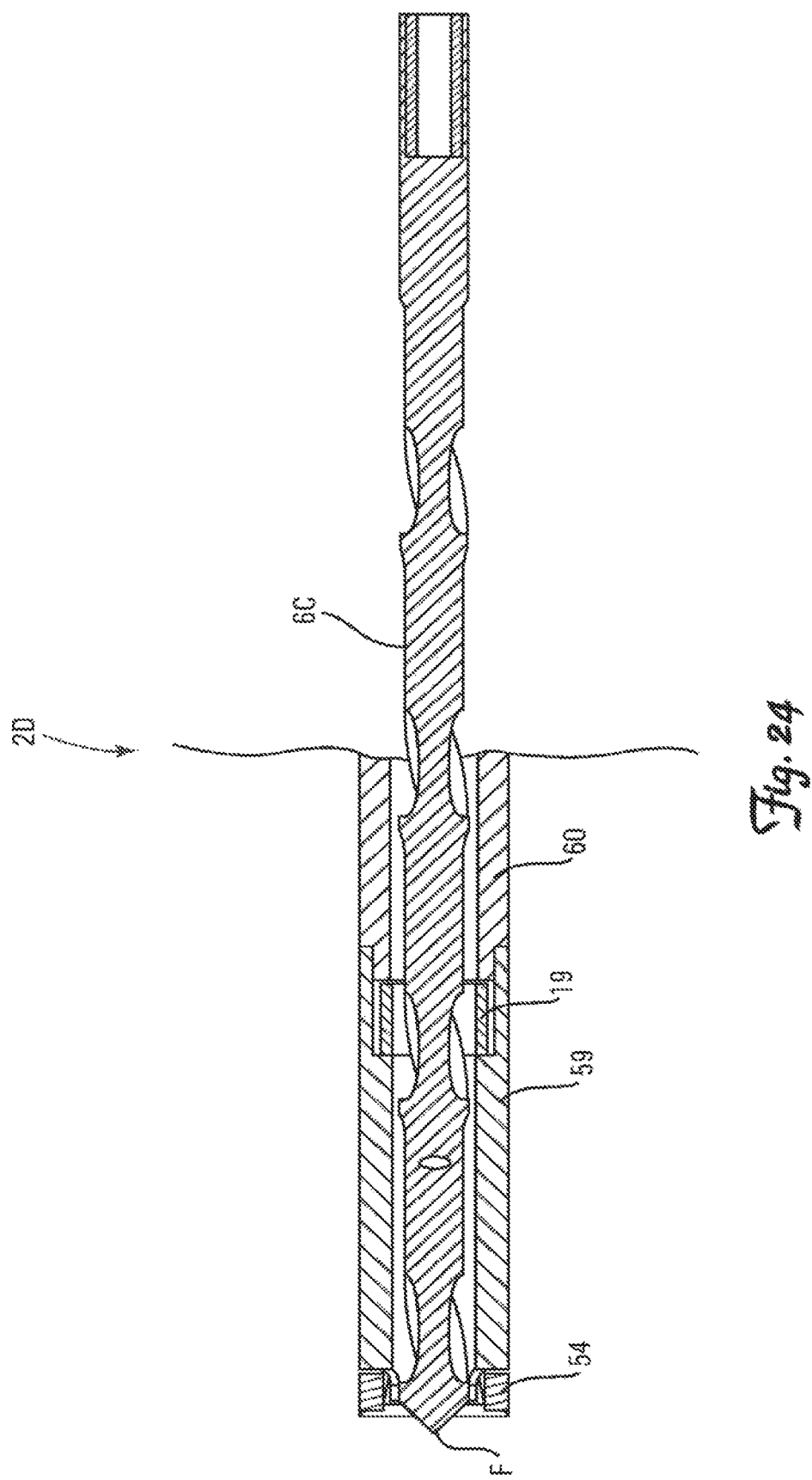
FIG. 24 is a side view of the atherectomy catheter of FIG. 23.
Figure 25:
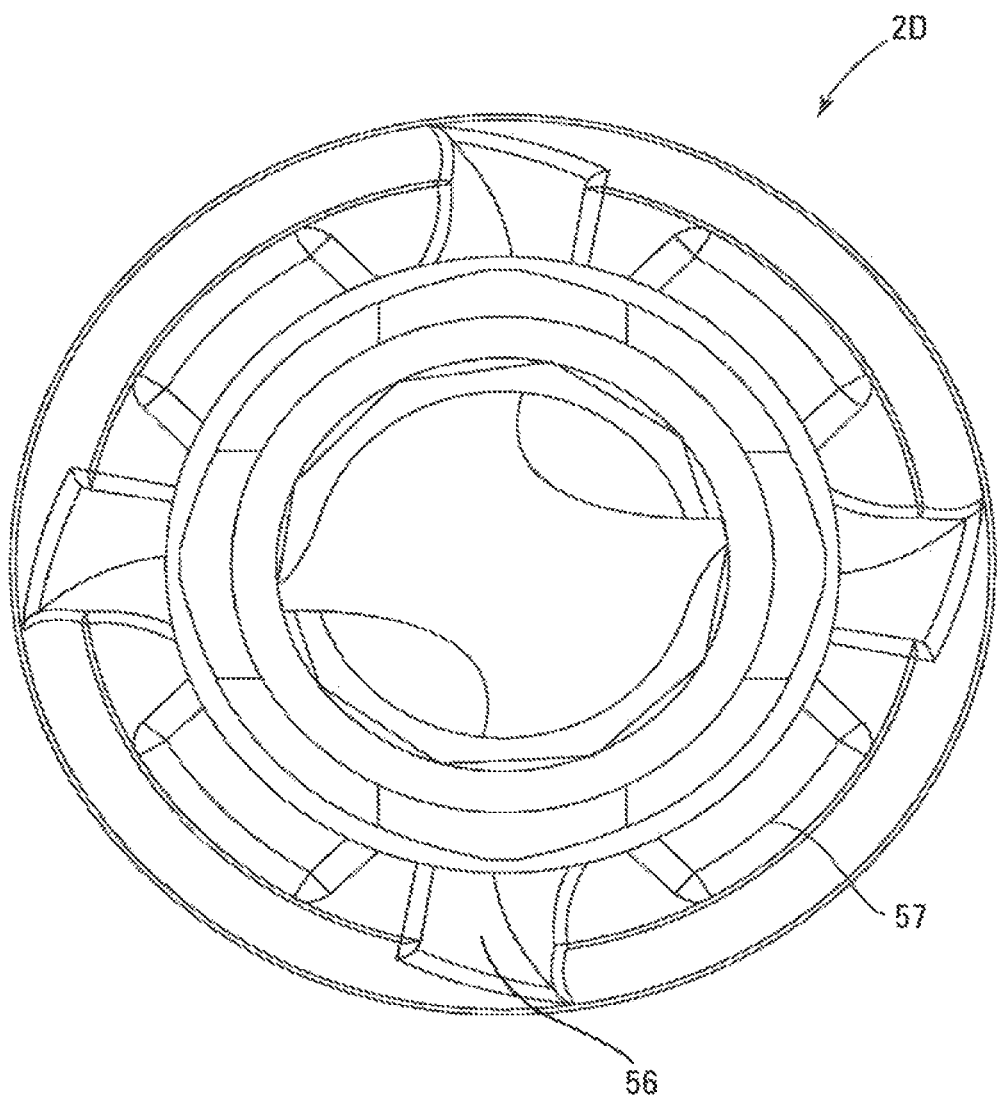
FIG. 25 is an end view of the atherectomy catheter of FIG. 23.

An alternative catheter embodiment is shown in FIGS. 23 to 25. Catheter 20 is shown wherein the same or similar reference numbers of catheter 2D refer to the same or similar structures of catheter 2 and all discussion concerning the same or similar features of catheter 2 are equally applicable here unless noted otherwise. Catheter 2D is similar to catheter 2C except that bushing 19 is positioned at a more proximal position and is housed in an annular slot formed in the inner wall surface of the outer cutter drive shaft. Bushing 19 is seated in the slot in a manner which allows the inner cutter drive shaft to rotate but which prevents either proximal or distal movement of the inner cutter drive shaft with respect to the outer cutter drive shaft. Bushing 19 is attached to the inner cutter drive shaft. Distal outer housing 59 and proximal outer housing 60 effectively capture bushing 19 between them to control the longitudinal position of the inner drive shaft in both proximal and distal directions and allows for the pieces to be assembled. In this example, cut tissue must pass under and through the open lumen of the assembly between the inner drive shaft and bushing 19, The outer drive shaft in this embodiment is connected to a cutting element 54 which is provided with teeth 56 and fins 57.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents. Further, while choices for materials and configurations may have been described above with respect to certain embodiments, one of ordinary skill in the art will understand that the materials and configurations described are applicable across the embodiments.

What is claimed is:

1. A catheter for removing tissue from a body lumen, the catheter comprising:
    an elongate sheath defining an interior;

an outer elongate shaft in the interior of the elongate sheath and having a longitudinal axis extending along the elongate sheath, the outer elongate member having an interior surface defining an interior;

an inner elongate shaft in the interior of the outer elongate shaft and having a longitudinal axis extending along the outer elongate shaft, the inner elongate shaft having an outer surface spaced apart radially relative to the longitudinal axis of the inner elongate shaft to define an annular space between the inner elongate shaft and the outer elongate shaft;

a tissue-removing element operatively connected to one of the outer elongate shaft and the inner elongate shaft, the tissue-removing element configured to direct removed tissue from the body lumen toward the annular space between the inner elongate shaft and the outer elongate shaft, wherein the outer elongate shaft is selectively rotatable about its longitudinal axis relative to the elongate sheath, wherein the catheter comprises a driver configured to drive the outer elongate shaft in continuous rotation about its longitudinal axis relative to the elongate sheath;

wherein the outer elongate shaft includes at least one projection extending radially inward relative to the longitudinal axis of the outer elongate shaft from the interior surface of the outer elongate shaft, wherein during rotation of the outer elongate shaft relative to the elongate sheath, the at least one projection is configured to at least one of: i) transport removed tissue in the annular space longitudinally along the annular space; and ii) break down removed tissue in the annular space wherein the outer elongate shaft has an overlapping longitudinal portion radially overlapping the inner elongate shaft, the overlapping longitudinal portion configured to rotate relative to the inner elongate shaft, and wherein the elongate sheath radially overlaps the overlapping longitudinal portion of the outer elongate shaft;

wherein the tissue-removing element is operatively connected to the inner elongate shaft.

2. The catheter set forth in claim 1, wherein the at least one projection comprises at least one shearing member and at least one helical rib.

3. The catheter set forth in claim 1, wherein during rotation of the outer elongate shaft relative to the elongate sheath, the at least one projection is configured to transport removed tissue in the annular space longitudinally along the annular space.

4. The catheter set forth in claim 1, wherein during rotation of the outer elongate shaft relative to the elongate sheath, the at least one projection is configured to break down removed tissue in the annular space.

5. The catheter set forth in claim 1, wherein the tissue-removing element is operatively connected to the outer elongate shaft.

6. The catheter set forth in claim 1, further comprising another tissue-removing element coupled to the outer elongate shaft.

7. The catheter set forth in claim 1, wherein the at least one projection comprises at least one shearing member.

8. The catheter set forth in claim 7, wherein the at least one shearing member follows a helical winding pattern.

9. The catheter set forth in claim 1, wherein the at least one projection comprises at least one helical rib.

10. The catheter set forth in claim 9, wherein the at least one helical rib is continuous and follows a helical winding pattern.

11. The catheter set forth in claim 1, further comprising a laminate over the outer elongate shaft.

12. The catheter set forth in claim 11, wherein the laminate comprises a polyester heat shrink tube.

13. The catheter set forth in claim 1, wherein the outer elongate shaft includes a coating on the interior surface thereof.

14. The catheter set forth in claim 13, wherein the coating comprises a lubricant.

15. The catheter set forth in claim 13, wherein the coating comprises an anticoagulant.

16. The catheter set forth in claim 1, wherein the inner elongate shaft is selectively rotatable about its longitudinal axis relative to the elongate sheath.

17. The catheter set forth in claim 16, wherein the inner elongate shaft includes a helical rib extending radially outward relative to the longitudinal axis of the inner elongate shaft from the outer surface of the inner elongate shaft.

18. The catheter set forth in claim 17, wherein the inner elongate shaft and the outer elongate shaft are rotatable in opposite directions.

19. A catheter for removing tissue from a body lumen, the catheter comprising:

an elongate sheath defining an interior;

an outer elongate shaft in the interior of the elongate sheath and having a longitudinal axis extending along the elongate sheath, the outer elongate member having an interior surface defining an interior;

an inner elongate shaft in the interior of the outer elongate shaft and having a longitudinal axis extending along the outer elongate shaft, the inner elongate shaft having an outer surface spaced apart radially relative to the longitudinal axis of the inner elongate shaft to define an annular space between the inner elongate shaft and the outer elongate shaft;

a tissue-removing element operatively connected to one of the outer elongate shaft and the inner elongate shaft, the tissue-removing element configured to direct removed tissue from the body lumen toward the annular space between the inner elongate shaft and the outer elongate shaft, wherein the outer elongate shaft is selectively rotatable about its longitudinal axis relative to the elongate sheath, wherein the catheter comprises a driver configured to drive the outer elongate shaft in continuous rotation about its longitudinal axis relative to the elongate sheath;

wherein the outer elongate shaft includes at least one projection extending radially inward relative to the longitudinal axis of the outer elongate shaft from the interior surface of the outer elongate shaft, wherein during rotation of the outer elongate shaft relative to the elongate sheath, the at least one projection is configured to at least one of: i) transport removed tissue in the annular space longitudinally along the annular space; and ii) break down removed tissue in the annular space wherein the outer elongate shaft has an overlapping longitudinal portion radially overlapping the inner elongate shaft, the overlapping longitudinal portion configured to rotate relative to the inner elongate shaft, and wherein the elongate sheath radially overlaps the overlapping longitudinal portion of the outer elongate shaft;

wherein the at least one projection comprises at least one shearing member;

wherein the at least one shearing member follows a helical winding pattern;

wherein the at least one shearing member comprises a plurality of discontinuous shearing members.

20. A catheter for removing tissue from a body lumen, the catheter comprising:

an elongate sheath defining an interior;

an outer elongate shaft in the interior of the elongate sheath and having a longitudinal axis extending along the elongate sheath, the outer elongate member having an interior surface defining an interior;

an inner elongate shaft in the interior of the outer elongate shaft and having a longitudinal axis extending along the outer elongate shaft, the inner elongate shaft having an outer surface spaced apart radially relative to the longitudinal axis of the inner elongate shaft to define an annular space between the inner elongate shaft and the outer elongate shaft;

a tissue-removing element operatively connected to one of the outer elongate shaft and the inner elongate shaft, the tissue-removing element configured to direct removed tissue from the body lumen toward the annular space between the inner elongate shaft and the outer elongate shaft, wherein the outer elongate shaft is selectively rotatable about its longitudinal axis relative to the elongate sheath, wherein the catheter comprises a driver configured to drive the outer elongate shaft in continuous rotation about its longitudinal axis relative to the elongate sheath;

wherein the outer elongate shaft includes at least one projection extending radially inward relative to the longitudinal axis of the outer elongate shaft from the interior surface of the outer elongate shaft, wherein during rotation of the outer elongate shaft relative to the elongate sheath, the at least one projection is configured to at least one of: i) transport removed tissue in the annular space longitudinally along the annular space; and ii) break down removed tissue in the annular space wherein the outer elongate shaft has an overlapping longitudinal portion radially overlapping the inner elongate shaft, the overlapping longitudinal portion configured to rotate relative to the inner elongate shaft, and wherein the elongate sheath radially overlaps the overlapping longitudinal portion of the outer elongate shaft;

wherein the at least one projection comprises at least one helical rib;

wherein the at least one helical rib is discontinuous to define a plurality of rib portions, wherein the rib portions follow a helical winding pattern.

* * * * *